(12) United States Patent
Walzman

(10) Patent No.: US 11,564,729 B2
(45) Date of Patent: Jan. 31, 2023

(54) TORUS BALLOON WITH ENERGY EMITTERS FOR INTRAVASCULAR LITHOTRIPSY

(71) Applicant: Daniel Ezra Walzman, Bergenfield, NJ (US)

(72) Inventor: Daniel Ezra Walzman, Bergenfield, NJ (US)

( * ) Notice: Subject to any disclaimer, the term of this patent is extended or adjusted under 35 U.S.C. 154(b) by 313 days.

(21) Appl. No.: 16/875,122

(22) Filed: May 15, 2020

(65) Prior Publication Data

US 2020/0337717 A1  Oct. 29, 2020

Related U.S. Application Data

(63) Continuation-in-part of application No. 16/870,045, filed on May 8, 2020, now Pat. No. 11,006,996, (Continued)

(51) Int. Cl.
| | |
|---|---|
| *A61B 17/22* | (2006.01) |
| *A61B 18/08* | (2006.01) |
| *A61B 18/00* | (2006.01) |
| *A61F 2/01* | (2006.01) |
| *A61M 25/00* | (2006.01) |

(52) U.S. Cl.
CPC ........ *A61B 18/082* (2013.01); *A61B 17/2202* (2013.01); *A61B 2017/22051* (2013.01); *A61B 2017/22079* (2013.01); *A61B 2018/00232* (2013.01); *A61B 2018/00244* (2013.01); *A61B 2018/00369* (2013.01); *A61B 2018/00714* (2013.01); *A61B 2217/007* (2013.01); *A61F 2/013* (2013.01); *A61M 25/007* (2013.01)

(58) Field of Classification Search
CPC .......... A61B 17/2202; A61B 17/22012; A61B 2017/22051; A61B 2017/22098
See application file for complete search history.

(56) References Cited

U.S. PATENT DOCUMENTS

| | | |
|---|---|---|
| 4,183,102 A | 1/1980 | Guiset |
| 4,309,994 A | 1/1982 | Grunwald |
| | (Continued) | |

FOREIGN PATENT DOCUMENTS

| | | |
|---|---|---|
| WO | WO 2005112823 | 12/2005 |

OTHER PUBLICATIONS

PCT/US2021/026523 International Search Report and Written Opinion (dated Jul. 22, 2021).

(Continued)

*Primary Examiner* — Diane D Yabut
(74) *Attorney, Agent, or Firm* — Neil D. Gershon

(57) ABSTRACT

A catheter for intraluminal lithotripsy including an outer wall, at least one balloon extending from the outer wall, the balloon having a first portion, a second portion proximal of the first portion and an intermediate portion between the first and second portions such that a transverse dimension of the intermediate portion is less than a transverse dimension of the first and second portions. The catheter includes a first lumen, at least one energy emitter mounted on the balloon for emitting energy to break down or soften calcium and a connector connecting the at least one energy emitter to an external energy source, the connector extending through the catheter.

18 Claims, 10 Drawing Sheets

Related U.S. Application Data which is a continuation-in-part of application No. 15/932,911, filed on May 18, 2018, now Pat. No. 10,799,674, which is a continuation-in-part of application No. 15/732,953, filed on Jan. 16, 2018, now Pat. No. 10,857,328.

(56) References Cited

U.S. PATENT DOCUMENTS

| | | |
|---|---|---|
| 4,573,966 A | 3/1986 | Weiki |
| 4,661,094 A | 4/1987 | Simpson |
| 4,755,176 A | 7/1988 | Patel |
| 4,784,638 A | 11/1988 | Ghajar |
| 4,795,427 A | 1/1989 | Helzel |
| 4,944,745 A | 7/1990 | Sogard et al. |
| 4,968,306 A | 11/1990 | Huss |
| 4,970,926 A | 11/1990 | Ghajar |
| 5,087,247 A | 2/1992 | Horn et al. |
| 5,147,302 A | 9/1992 | Euteneuer et al. |
| 5,163,905 A | 11/1992 | Don Michael |
| 5,163,910 A | 11/1992 | Schwartz et al. |
| 5,167,628 A | 12/1992 | Boyles |
| 5,180,387 A | 1/1993 | Ghajar |
| 5,284,473 A | 2/1994 | Calabria |
| 5,344,402 A | 9/1994 | Crocker |
| 5,370,617 A | 12/1994 | Sahota |
| 5,411,479 A | 5/1995 | Bodden |
| 5,460,610 A | 10/1995 | Don Michael |
| 5,470,314 A | 11/1995 | Insky |
| 5,478,309 A | 12/1995 | Sweezer et al. |
| 5,540,707 A | 7/1996 | Ressemann et al. |
| 5,542,925 A | 8/1996 | Orth |
| 5,613,980 A | 3/1997 | Chauhan |
| 5,639,274 A | 6/1997 | Fischell et al. |
| 5,669,924 A | 9/1997 | Shaknovich |
| 5,720,735 A | 2/1998 | Dorros |
| 5,769,828 A | 6/1998 | Jonkman |
| 5,800,407 A | 9/1998 | Eldor |
| 5,830,181 A | 11/1998 | Thornton |
| 5,840,066 A | 11/1998 | Matsuda |
| 5,919,163 A | 7/1999 | Glickman |
| 5,928,181 A | 7/1999 | Coleman et al. |
| 5,947,985 A | 9/1999 | Imran |
| 5,951,514 A | 9/1999 | Sahota |
| 5,954,687 A | 9/1999 | Baudino |
| 6,013,054 A | 1/2000 | Jiun Yan |
| 6,017,324 A | 1/2000 | Tu |
| 6,048,333 A | 4/2000 | Lennox |
| 6,071,285 A | 6/2000 | Lashinski |
| 6,086,557 A | 7/2000 | Morejohn |
| 6,129,704 A | 10/2000 | Forman et al. |
| 6,146,370 A | 11/2000 | Barbut |
| 6,193,685 B1 | 2/2001 | Goodin |
| 6,223,637 B1 | 5/2001 | Hansen |
| 6,296,655 B1 | 10/2001 | Gaudoin et al. |
| 6,364,900 B1 | 4/2002 | Heuser |
| 6,514,281 B1 | 2/2003 | Blaeser |
| 8,403,911 B2 | 3/2013 | Adams et al. |
| 8,460,240 B2 | 6/2013 | Towler |
| 8,480,619 B2 | 7/2013 | Porter |
| 8,485,961 B2 | 7/2013 | Campbell et al. |
| 8,496,629 B2 | 7/2013 | McKinnon |
| 8,747,456 B2 | 6/2014 | Bairn |
| 8,951,226 B2 | 2/2015 | Hameed |
| 8,956,383 B2 | 2/2015 | Aklog |
| 9,295,818 B2 | 3/2016 | Riina |
| 9,364,634 B2 | 6/2016 | Adams |
| 9,399,112 B2 | 7/2016 | Shevgoor |
| 9,440,043 B2 | 9/2016 | Arora |
| 9,579,494 B2 | 2/2017 | Kersten et al. |
| 9,642,673 B2 | 5/2017 | Adams et al. |
| 9,993,325 B2 | 6/2018 | Ren |
| 10,299,824 B2 | 5/2019 | Walzman |
| 10,328,246 B1 | 5/2019 | Walzman |
| 10,314,684 B2 | 6/2019 | Walzman |
| 10,576,245 B2 | 3/2020 | Walzman |
| 10,610,672 B2 | 4/2020 | Walzman |
| 10,799,674 B2 | 10/2020 | Walzman |
| 2002/0035361 A1* | 3/2002 | Houser ............... A61B 18/00 606/7 |
| 2002/0052620 A1 | 5/2002 | Barbut |
| 2002/0165572 A1 | 11/2002 | Saadat |
| 2002/0188276 A1 | 12/2002 | Evans |
| 2003/0023204 A1 | 1/2003 | Vo |
| 2003/0097169 A1 | 5/2003 | Brucker |
| 2003/0198798 A1 | 10/2003 | Hehrlein |
| 2004/0006306 A1 | 1/2004 | Evans |
| 2004/0024347 A1 | 2/2004 | Wilson |
| 2004/0059278 A1 | 3/2004 | McPherson |
| 2004/0122465 A1 | 6/2004 | McMurtry |
| 2005/0038420 A1 | 2/2005 | Huybregts |
| 2005/0171505 A1 | 8/2005 | Bertolero |
| 2006/0235459 A1 | 10/2006 | Das |
| 2007/0038170 A1 | 2/2007 | Joseph |
| 2007/0185445 A1 | 8/2007 | Nahon |
| 2007/0197997 A1 | 8/2007 | Dua |
| 2007/0225750 A1* | 9/2007 | Ren ............... A61F 2/013 606/200 |
| 2007/0287967 A1 | 12/2007 | Hekmat |
| 2008/0039786 A1 | 2/2008 | Epstein |
| 2008/0125746 A1 | 5/2008 | Shapland |
| 2008/0281394 A1 | 11/2008 | Jones |
| 2009/0209855 A1 | 8/2009 | Drilling |
| 2009/0209907 A1 | 8/2009 | Grata |
| 2010/0016862 A1* | 1/2010 | Hawkins ............ A61B 17/2202 606/128 |
| 2011/0190727 A1 | 8/2011 | Edmunds |
| 2011/0245802 A1 | 10/2011 | Hayman |
| 2011/0276023 A1 | 11/2011 | Leeflang |
| 2012/0029436 A1 | 2/2012 | Yassinzadeh |
| 2012/0116352 A1 | 5/2012 | Rangi |
| 2012/0136242 A1 | 5/2012 | Qi |
| 2012/0253358 A1* | 10/2012 | Golan ............... A61B 17/221 606/128 |
| 2012/0302953 A1 | 11/2012 | Don Michael |
| 2012/0316632 A1 | 12/2012 | Gao |
| 2013/0116714 A1* | 5/2013 | Adams ............ A61B 17/22022 606/159 |
| 2013/0158511 A1 | 6/2013 | Aggerholm |
| 2013/0190796 A1 | 7/2013 | Tilson et al. |
| 2014/0025151 A1 | 1/2014 | Gao |
| 2014/0148751 A1 | 5/2014 | Kassab et al. |
| 2015/0127034 A1 | 5/2015 | Eaton |
| 2015/0196303 A1 | 7/2015 | Seguin |
| 2016/0278783 A1 | 9/2016 | Magee |
| 2016/0324668 A1 | 11/2016 | Wallace et al. |
| 2017/0000493 A1 | 1/2017 | Boehm |
| 2017/0007800 A1 | 1/2017 | Chao et al. |
| 2017/0086860 A1 | 3/2017 | Lee |
| 2018/0126130 A1 | 5/2018 | Nitzan et al. |
| 2018/0161552 A1 | 6/2018 | Larson |
| 2018/0229010 A1 | 8/2018 | Walzman |
| 2019/0217049 A1 | 7/2019 | Walzman |
| 2019/0217050 A1 | 7/2019 | Walzman |
| 2019/0217051 A1 | 7/2019 | Walzman |
| 2019/0217069 A1 | 7/2019 | Walzman |
| 2019/0321602 A1 | 10/2019 | Walzman |
| 2020/0281623 A1 | 9/2020 | Walzman |

OTHER PUBLICATIONS

PCT/US2021/026521 International Search Report and Written Opinion (dated Aug. 5, 2021).
U.S. Appl. No. 15/258,877, filed Sep. 2016, Walzman.

* cited by examiner

TORUS BALLOON WITH ENERGY EMITTERS FOR INTRAVASCULAR LITHOTRIPSY

This application is a continuation in part of application Ser. No. 16/870,045, filed May 8, 2020, which is continuation in part of application Ser. No. 15/932,911, filed May 18, 2018, which is a continuation in part of application Ser. No. 15/732,953, filed Jan. 16, 2018. The entire contents of each of these applications are incorporated herein by reference.

BACKGROUND OF THE INVENTION

1. Field of the Invention

The present invention relates generally to a catheter placed in a minimally invasive manner, and, more particularly, to a catheter having a torus balloon with energy emitters for intravascular lithotripsy.

2. Background of the Related Art

The use of devices in conjunction with medical procedures for controlling blood flow in a blood vessel is taught by the prior art. Among the most common is a balloon catheter. The balloon catheter, such as taught in the prior art, may be used to achieve isolation of a body part from its blood supply as the balloon is inflated (expanded) to occupy the vessel space and block blood flow.

One of the problems associated with using balloons is that although control of the blood flow through a portion of the blood vessel is achieved, including blockage of the blood supply to a targeted site, blood flow is completely interrupted to other sites near the targeted site. This shortcoming can be tolerated for a short duration because when one blood vessel becomes blocked, the body normally increases the blood flow through other, essentially paralleling blood vessels. However, such interruption of blood flow becomes problematic when used for a longer duration. That is, complex medical procedures may not be achieved during said short duration resulting in injury to other sites or requiring multiple operations at the same targeted site. The need exists for a device for better controlling blood flow during the surgical procedure.

Additionally, current bypass catheters are designed to be surgically implanted, which is not practical for immediate relief of progressive ischemia caused by a sudden blockage of a blood vessel, such as from a thrombus or embolus.

Various devices are known for performing thrombectomy, i.e., removal of a blood clot from a vessel. These include for example mechanical thrombectomy devices with rotational element(s) to break up the clot, devices that deliver thrombolytics to dissolve blood clots, devices that delivery vibrational energy in the form of continuous or pulsating waves, etc. However, these devices do not provide for adequate controlling of blood flow during the procedure. Furthermore, these procedures can often be lengthy, and most often do not provide immediate restoration of flow to the ischemic territory.

It would be advantageous to provide for control of blood flow during removal or treatment of a blood clot or other blockages or removal or softening calcifications. This would be particularly advantageous in procedures where the procedure is of relatively long duration, such as in the use of thrombolytics wherein the blood clot lyses from lytic infusion over time, since it would provide immediate and continuous reperfusion. It is further advantageous to provide immediate restoration of downstream blood flow, allowing time for amelioration of a blockage while stopping further progression of ischemic injury to the involved vascular territory. None of the current devices achieves this.

SUMMARY OF THE INVENTION

The present invention overcome the problems and deficiencies of the prior art. The present invention provides an improved catheter and method for use in the vascular system of the body and surmounts the problem of complete blood interruption that causes ischemia, which if not rapidly reversed will result in permanent injury. That is, the present invention is deployed to address a clot or other blockage in an artery or vein that is causing ischemia or heart strain because of the lack of flow through.

Additionally, the present invention provides in some embodiments an improved catheter and method of use for intraluminal lithotripsy, and in certain applications for softening the calcium of a highly calcified valve, such as a cardiac valve.

The present invention provides in some aspects a bypass catheter, placed in the body temporarily, i.e., during the surgical procedure, or for a fixed period of time, having a distal opening (hole) and more proximal intravascular opening (hole) that enables blood flow from a region proximal of the blood clot to a region distal of the clot during the clot treatment procedure. Various embodiments of the bypass catheters are disclosed herein, which include different devices for treating/removing blood clots. In some embodiments, the catheter also includes structure that limits retrograde blood flow through the catheter to enhance the reperfusion function of the catheter. In some embodiments, the catheter includes a filter at a distal portion to capture or block particles.

The present invention in some embodiments includes a temporary bypass balloon mounted catheter, a single lumen difficult access support catheter, and a rotating irrigating and aspirating thrombectomy device. These are disclosed in application Ser. No. 15/732,397 (temporary bypass balloon catheter); and application Ser. Nos. 15/258,877, 15/538,898, and 15/731,478 (rotating separator, irrigator microcatheter for thrombectomy); and other Walzman single-lumen support disclosures, and the present invention in these embodiments provides an improvement thereof.

The devices of the present invention are capable of being positioned so that at least one or more proximal holes, e.g., one or more side holes, of the device is located on one side of said artery or vein clot/blockage and a more distal hole (or holes), e.g., a distal end hole, of the device is located on the other side of the said artery or vein clot/blockage. Once the device is positioned in the desired region in the vessel, a bypass element of the device allows temporary bypass of flow through the catheter, e.g., through the first or distal segment of the catheter as described below.

In some embodiments, in order to prevent backflow of the blood into the catheter, i.e., into a segment (region) of the catheter proximal of the side hole, structure is provided to restrict back flow. Various embodiments of such structure are disclosed herein and include a valve to provide flow in one direction (distal direction), a smaller (reduced) proximal diameter, or attachment to a pressurized fluid line, or a combination of the above. These are discussed in more detail below.

Moreover, in some embodiments, the catheter of the present invention can have an additional lumen extending in the wall, or substantially in the wall, of the intravascular segment of the catheter, in addition to or instead of the lumen for delivering fluid into a balloon for inflation thereof which can extend in the wall, or substantially in the wall, of the catheter, which would deliver fluid into the clot between the side hole and the end hole via at least one perforation that communicates with the inside of the vessel. This would allow delivery of lytics or other such medications into the clot while there is an effective temporary bypass of flow through the catheter, allowing time for the directly applied medication to break up the clot and dissolve the clot while avoiding progressive ischemic tissue injury during the interim time.

In some embodiments, a balloon (or other anchoring structure) is provided on the outer diameter (outer wall) of the catheter, and the catheter can include an additional lumen within the wall, or substantially within the wall, of the intravascular segment of the catheter for inflation and deflation of the balloon.

Moreover, in some embodiments, a mechanical thrombectomy structure can be provided for breaking up the clot such as side loops as described below that can macerate the clot when rotated.

In some embodiments, aspiration can also be applied to the catheter, which can allow aspiration through the side hole and or through the end hole. If aspiration through the end hole only is desired, then the side hole can be withdrawn into a sheath or otherwise covered, as described below, so that the side hole is blocked and there is no aspiration on the side hole and all aspiration forces are on the end hole. Alternatively, an actively controlled valve can be provided to close the side hole.

There is a critical advantage to the devices of the present invention in that they allow rapid restoration of temporary flow of blood through a blockage to avoid ischemic injury, with immediate restoration of a degree of flow beyond a clot. This will allow additional time to remove or dissolve the clot while allowing flow to the at-risk tissue. Additionally, in the case of pulmonary emboli which are large, there is an additional issue of heart strain due to the lack of outflow from the right side of the heart. The temporary bypass catheters described herein can also help relieve such heart strain by allowing outflow from the right heart past said clot when there are large pulmonary emboli in the main pulmonary arteries.

In accordance with one aspect of the present invention, a surgical apparatus (device) for treating a blood clot or other blockage in a vessel of a patient is provided comprising an elongated member, preferably tubular, having an outer wall, a first opening (hole) at a distal portion and a second opening (hole) spaced proximally from the distal hole. The second hole is preferably positioned in a side of the outer wall. A first lumen within the elongated member is provided for blood flow through the proximal second hole, through the first lumen and exiting the distal first end hole to maintain blood flow during treatment of the blood clot. In some embodiments, the first lumen is a single primary central lumen.

At least one perforation can be positioned between the first hole and the second hole. A second lumen within the wall, substantially within the wall or within the primary lumen of the intravascular segment communicates with the at least one perforation. The second lumen forms a channel for injection of fluid through the at least one perforation into the vessel to treat the blood clot, wherein blood flows into the second hole positioned proximal of the blood clot and exits the first hole distal of the blood clot during injection of the fluid to treat the blood clot.

In some embodiments, there is at least one additional third proximal end-hole, which has an external termination device attached, and remains outside the patient's body at all times. Aspiration can optionally be applied to the third proximal end-hole when desired, to remove clot and debris from the vessel.

In some embodiments, the elongated member has at least one energy emitting element positioned thereon, and in some embodiments they are within or substantially within the wall of said elongate member, to emit energy to aid breakdown and removal of the blood clot. In some embodiments, the energy emitting elements are positioned between the first and second holes of the catheter. In some embodiments, the energy emitting elements comprise ultrasound radiating elements to enhance flow or mixing of the fluid (drug) injected from the catheter into or adjacent the blood clot. In some embodiments, the ultrasound emission of the radiating elements is synchronized with timing of delivery of the fluid. In some embodiments, the energy may directly break up larger pieces of clot. In some embodiments, the energy may help break up, soften, and dissolve calcifications and other hardenings. In some embodiments, cooling elements may be present. In some embodiments, heating elements may be present.

In some embodiments, at least one connector is provided to connect the energy emitters to an energy source for application of energy to the blood clot or other blockage to aid treatment, e.g., removal/dissolution of the blood clot. In some embodiments, the at least one connector is configured to connect the apparatus to an ultrasonic energy source. In some embodiments, the energy emitting elements extend within the wall of the catheter. In some embodiments, the energy emitting elements extend on at least a portion of the surface of the catheter. In some embodiments, the energy emitting elements may be incorporated into at least one balloon extending from the catheter. Such embodiments may be of particular use during intravascular lithotripsy of a cardiac valve or intracranial vessel, where prolonged balloon inflation is optimal for the optimal contact and treatment time might not be tolerated without a bypass element allowing egress of blood from the heart and perfusion of the cerebral vascular territory, respectively.

The foregoing energy source and energy emitters may also be utilized in the bulging torus balloon, disclosed in U.S. Pat. No. 10,328,246, the entire contents of which are hereby incorporated herein by reference. Such device can be used during valve lithotripsy while allowing egress of blood from the heart through the central hole of the torus balloon, during prolonged balloon inflation for prolonged contact with the valve, or similarly continued blood flow through a vessel during use in a vessel.

In some embodiments, the apparatus includes a rotatable macerator element positioned between the first and second holes, the macerator element rotatable to break up blood clot and other intravascular debris and blockages.

In some embodiments, the apparatus includes a sheath positioned over the elongated member, the elongated member and sheath relatively movable to selectively cover and expose the side hole, wherein covering of the side hole restricts flow of blood through the side hole. In some embodiments, covering of the hole completely blocks flow of fluid through said side hole.

In some embodiments, the apparatus has features to restrict retrograde blood flow within said catheter such as a valve or a reduced diameter region for the first lumen. In some embodiments, attaching pressurized fluid to the catheter at a proximal region can restrict retrograde blood flow within said catheter.

It should be noted that in some embodiments where there is an additional lumen that courses through the intravascular segment of the elongate body, the device divides proximally into multiple lumens with independent outer walls, preferably outside of the patient's body. Preferably, each lumen ends at its proximal end-hole with an independent external termination device, such as a hub with a luer-lock or diaphragm.

In accordance with another aspect of the present invention, a surgical apparatus (device) for treating a blood clot or other blockage in a vessel of a patient is provided comprising an elongated member having an outer wall, a first opening (hole) at a distal portion and a second openings (hole) spaced proximally from the distal opening. The second hole is preferably positioned in a side of the outer wall. A first lumen within the elongated member provides for blood flow through the proximal hole, through the lumen and exiting the distal first hole to maintain blood flow during treatment of the blood clot. The apparatus includes at least one energy emitter for emitting energy to the blood clot and a connector extending through the elongated member to connect the energy emitter to an external energy source, wherein blood flows into the second hole positioned proximal of the blood clot and exits the first hole distal of the blood clot once the bypass segment is positioned across the blockage. In this position, activation of the energy emitter can also be utilized. In this position, infusion of medications can also be utilized.

In some embodiments, the energy emitter is positioned between the first and second holes. In some embodiments, the energy emitter emits ultrasonic energy to the blood clot. In some embodiments, a switch on the apparatus is provided to activate the energy emitters. In some embodiments, a switch external to the apparatus can activate the energy emitters.

In some embodiments, the apparatus further comprises a second lumen for delivering medication to the blood clot for dissolving the blood clot. In some embodiments, this occurs during application of ultrasonic energy.

In accordance with another aspect of the present invention, a method for treating a blood clot or other blockage in a vessel of a patient is provided comprising the steps of a) inserting into the vessel a device (apparatus) having a first opening (hole) at a distal portion and a second opening (hole) spaced proximally from the distal hole, the second hole positioned in a side of the outer wall; b) positioning the second hole of the device proximal of the blood clot and the first hole of the device distal of the blood clot to thereby enable blood flow through the proximal hole, through the first lumen and exiting the distal hole to maintain blood flow during treatment of the blood clot; and c) during blood flow through the lumen, applying energy to energy emitters carried by the device to apply energy to the blood clot.

In some embodiments, the method further comprises the step of injecting a thrombolytic fluid through one or more perforations in a side wall of the device.

In some embodiments, the method further comprises the step of selectively blocking blood flow through the second hole and aspirating clot through the first hole, via an external aspirator applied to a third hole, i.e., a proximal end hole external to the patient's body.

In some embodiments, the method further comprises the step of injecting a thrombolytic fluid through one or more perforations in a side wall of the device.

In some embodiments, the method further comprises the step of selectively blocking blood flow through the second hole during subsequent aspiration.

In some embodiments, the device has at least one balloon on the external surface of the elongate member overlying said first lumen. In some embodiments, the device further comprises at least one energy emitter on or carried/supported by the balloon for emitting energy.

In some embodiments, the method further comprises the step of using the device as described herein and advancing the device across a valve, inflating the balloon, while blood flows through the first lumen in either direction needed while the balloon is inflated, activating the energy to break up and soften hardenings in and around the valve, deactivating the energy and deflating the balloon.

In some embodiments, the hardenings are calcifications.

In some embodiments, inflation, energy emission, and deflation, are repeated at least two times.

In some embodiments the method includes the step of rotational maceration prior to aspiration.

In accordance with another aspect of the present invention, a catheter is provided having balloon carrying (supporting) or mounting one or more energy emitters for treating blockages. The balloon has a passageway for blood flow. More specifically, the catheter can have a torus balloon for energy delivery and can have a single lumen therein, which can allow passage of a wire, fluid injections, and/or fluid for inflation of the balloon. In other embodiments, the catheter mounted torus balloon for energy delivery can have a single catheter lumen exclusively for the balloon. In other embodiments, the catheter mounted torus balloon for energy delivery may have more than one catheter lumen. There may be a single balloon or multiple balloons. A balloon can be on any segment of the catheter. In some embodiments, the energy emitting elements may extend onto the outer surface of at least one balloon.

In accordance with another aspect of the present invention, a catheter for intraluminal lithotripsy is provided having an outer wall, at least one torus balloon mounted on the outer wall, a first lumen extending therein, at least one energy emitter for emitting energy to break down calcium, the at least one energy emitter mounted on the balloon and a connector connecting the energy emitter to an external energy source, the connector extending through the catheter.

In some embodiments, the catheter is capable of prolonged inflation of the at least one torus balloon within a cardiac valve, without critically obstructing cardiac outflow. In some embodiments, the catheter is capable of prolonged inflation of the at least one torus balloon within a vessel, without critically obstructing blood flow. Thus, the opening in the torus balloon allows blood flow while the balloon is inflated which in the absence of such opening would cut off flow as the inflated balloon fills the vessel lumen. In preferred embodiments, the balloon is inflated so the energy emitters are in contact with the target tissue, e.g., the calcifications in the vessel lumen.

In some embodiments, the catheter includes a second lumen, wherein the first lumen is dedicated solely for the inflation and deflation of the torus balloon.

In some embodiments, the catheter includes a plurality of energy emitters spaced apart on the torus balloon. In some embodiments, the at least one energy emitter comprises a plurality of ultrasound radiating elements.

In some embodiments, the torus balloon has an opening to provide passage of blood therethrough. The torus balloon in some embodiments can be offset from a longitudinal axis of the catheter so a majority of the balloon is offset to one side of the longitudinal axis, and the passage in the balloon is parallel to the longitudinal axis of the catheter. In some embodiments, the torus balloon has a channel to receive the catheter, the channel radially spaced from the passage.

In some embodiments, the torus balloon has an outer surface extending circumferentially, and a passage of the torus balloon is parallel to a longitudinal axis of the catheter, the at least one energy emitter including a plurality of energy emitters on the circumference of the torus balloon to apply energy radially from the circumference of the balloon.

In some embodiments, the catheter includes a filter positioned distal of the torus balloon to capture particles. The filter can be provided on the other catheters disclosed herein.

In accordance with another aspect of the present invention, a method of valve lithotripsy is provided including the steps of introducing the foregoing torus balloon across a valve, inflating the torus balloon, emitting energy over a period of time, subsequently stopping emitting energy, deflating the balloon, and removing the catheter.

In some embodiments, the inflation, emitting of energy, and deflation, are repeated at least two times prior to removal of the catheter.

In accordance with another aspect of the present invention, a catheter for intraluminal lithotripsy is provided comprising an outer wall and at least one balloon extending from the outer wall, the balloon having a first portion, a second portion proximal of the first portion and an intermediate portion between the first and second portions. A transverse dimension of the intermediate portion is less than a transverse dimension of the first and second portions. The catheter has a first lumen, at least one energy emitter carried/ supported or mounted on the balloon for emitting energy to break down or soften calcium and a connector connecting the at least one energy emitter to an external energy source, the connector extending through the catheter.

In preferred embodiments, the balloon is a torus balloon. In some embodiments, the balloon has figure eight configuration.

In some embodiments, the catheter is capable of prolonged inflation of the balloon within a cardiac valve, without critically obstructing cardiac outflow.

In some embodiments, the at least one energy emitter includes an energy emitter on the second portion of the torus balloon facing the first portion and at least one energy emitter on the first portion of the torus balloon facing the second portion. In some embodiments, the first and second portions are configured to press against opposing sides of the cardiac valve. In some embodiments, the intermediate portion of the balloon forms a waist portion creating a gap between the first and second portions of the torus balloon. The waist portion can be configured for positioning in an orifice of a cardiac valve and the first and second portions of the torus balloon press against opposing sides of the cardiac valve, e.g., press against the sides of the valve leaflets.

In some embodiments, the balloon has an opening to provide a passage for blood therethrough. In some embodiments, the balloon is offset from a longitudinal axis of the catheter so a majority of the balloon is offset to one side of the longitudinal axis, and the passage is parallel to the longitudinal axis. In some embodiments, the balloon has a channel to receive the catheter, the channel radially spaced from the opening in the balloon.

In some embodiments, the catheter has a filtering member positioned distal of the balloon to capture particles.

In some embodiments, the catheter has an outer wall, a lumen, a first hole at a distal portion positioned distal of the balloon and a second hole spaced proximally from the first hole and positioned proximal of the balloon and positioned in a side of the outer wall, wherein blood flows through the second hole, through the first lumen and exits the first hole while the balloon is inflated and energy is emitted by the at least one energy emitter.

In some embodiments, an axially slidable member is slidable relative to the catheter, the catheter and sliding member relatively movable to selectively cover and expose the second hole, wherein covering of the second hole restricts flow of blood through the second hole.

In some embodiments, the catheter includes a valve to restrict retrograde blood flow through the elongated member.

In some embodiments, the energy emitter applies ultrasonic energy.

In accordance with another aspect of the present invention, a method for reducing calcium at a cardiac valve of a patient is provided comprising:
  a) inserting into the vessel a device having at least one balloon extending from the outer wall, the balloon having a first portion, a second portion proximal of the first portion and an intermediate portion between the first and section portions, a transverse dimension of the intermediate portion being less than a transverse dimension of the first and second portions of the balloon, and at least one energy emitter on the first portion of the balloon and at least one energy emitter on the second portion of the balloon;
  b) positioning the balloon adjacent the cardiac valve so the first portion faces a first side of the valve and a second portion faces a second opposing side of the valve and the intermediate portion is positioned in a valve orifice; and
  c) applying energy to the at least one energy emitter to apply energy to the first and second sides of the cardiac valve to break down or soften calcium.

In some embodiments, the balloon is a torus balloon and is offset from a longitudinal axis of the catheter and has an opening offset from the longitudinal axis of the catheter for passage of blood therethrough to pass the cardiac valve.

In some embodiments, the balloon is a torus balloon and the catheter has an outer wall, a lumen, a first hole at a distal portion positioned distal of the torus balloon and a second hole spaced proximally from the first hole and positioned proximal of the torus balloon and positioned in a side of the outer wall, wherein blood flows through the second hole, through the first lumen and exits the first hole while the torus balloon is inflated to bypass the cardiac valve.

In some embodiments, the balloon is a torus balloon, and the torus balloon is inflated to fill a lumen of the vessel and the first portion presses against the first side of the cardiac valve and the second portion presses against the second side of the cardiac valve, and blood bypasses the inflated balloon as the energy emitters apply energy to the first and second sides of the cardiac valve.

BRIEF DESCRIPTION OF THE DRAWINGS

The invention will be better understood and objects other than those set forth above will become apparent when consideration is given to the following detailed description thereof. Such description makes reference to the annexed drawings wherein.

DETAILED DESCRIPTION OF THE INVENTION

Figure 1:
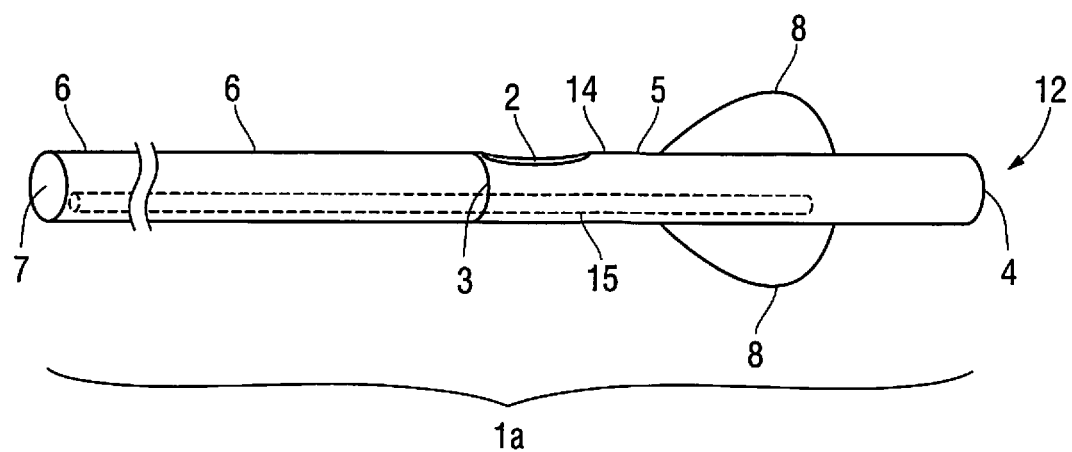
FIG. 1 is a side view of one embodiment of the bypass catheter of the present invention.

The present invention provides a catheter and method for use in the blood vessel of a patient during a blood clot treatment procedure. The catheter advantageously provides for blood flow during various clot treatment/removal procedures such as mechanical thrombectomy utilizing rotational element(s) to break up the clot, devices that deliver thrombolytics to dissolve blood clots, devices that delivery vibrational energy in the form of continuous or pulsating waves, devices that deliver energy to aid and/or effect blood clot removal, etc., as well as combinations thereof. These various embodiments are described in detail below.

The devices of the present invention provide for controlling blood flow during the procedure to thereby enable immediate and, if desired, continuous, reperfusion during the procedure. They allow rapid restoration of temporary flow of blood through a blockage to avoid ischemic injury, with immediate restoration of a degree of flow beyond a clot. This allows additional time to treat, e.g., remove or dissolve the clot or other blockage, while allowing flow to the at-risk tissue.

Additionally, in the case of pulmonary emboli which are large, there is an additional issue of heart strain due to the lack of outflow from the right side of the heart. The temporary bypass catheters described herein can also help relieve such heart strain by allowing outflow from the right heart past said clot when there are large pulmonary emboli in the main pulmonary arteries.

The present invention provides in some embodiments a catheter for use for intraluminal lithotripsy, and in certain applications for softening the calcium of a highly calcified valve, such as a cardiac valve, as described in more detail below.

In general, the devices of the present invention achieve such reperfusion by provision of a catheter deployed across a blockage in the vessel. The catheter in some embodiments is a bypass catheter having a distal opening and at least one proximal intravascular opening providing a bypass window, the openings positioned within vessel(s) on either side of the blood clot to be treated as the catheter is positioned across the blockage in the vessel. This enables blood flow from a region proximal of the clot to a region distal of the clot. In some embodiments, the catheter includes additional structure or features that limit retrograde blood to enhance the reperfusion function of the catheter. These various structures/features are discussed in detail below.

In some embodiments, the present invention utilizes in an improvement thereof elements of a temporary bypass catheter and balloon, a single lumen support catheter, and a rotating irrigating and aspirating thrombectomy device.

In some embodiments the device may further comprise a semipermeable filter attached circumferentially at or near its distal end to minimize the risk of emboli during the procedure. The filter can be self-expanding. The filter may have various modalities, to constrain and deploy it as desired. In some embodiments, the filter can be attached to a wire that extends through the entire lumen of the device and deploys distally within the vessel. In some embodiments, the filter is distal to the distal end hole and is tethered to the catheter.

Referring now to the drawings and particular embodiments of the present disclosure, wherein like reference numerals identify similar structural features of the devices disclosed herein throughout the several views, there are illustrated several embodiments of the catheters of the present invention.

Note as used herein, the term "proximal" and "distal" refer to the direction of blood flow with blood flowing in a proximal to distal direction. Also note the terms "apparatus"

and "device" and "catheter" are used interchangeably herein. Also note the terms "hole" and "opening" are used interchangeably herein.

"Blood clot treatment" as used herein includes any type of treatment of the blood clot which can include partial removal of the clot, reduction in size of the clot, complete removal of the clot, removal by mechanical thrombectomy, dissolution by medication, etc. The devices of the present invention can also be used for other vascular treatment including removal of other intravascular debris and blockages as well. Thus, the terms "blood blockage treatment" or "vessel blockage treatment" as used herein include blockage due to clots or other blockages.

Referring now to FIG. 1, a first embodiment of the bypass catheter of the present invention is illustrated. Note the catheters disclosed herein are also referred to as a device or apparatus. The catheter, designated generally by reference numeral (1a), is in the form of an elongated member, preferably tubular, and has a proximal hole (7), which in some embodiments is attached to an external termination device, a distal end hole (4) at a distal portion and a side hole (bypass window) (2) disposed upon the outer diameter, i.e., in the wall (14) of the device (1) at the juncture of first (distal) segment (5) and second (proximal) segment (6). Note the segments (5) and (6) indicate the two regions or portions of the catheter (1a) as the catheter (1a) can be an integral tubular structure as shown. However, alternatively, the segments (5) and (6) can be composed of separate elongated tubular members that are attached/joined together. Side hole (2) defines the end of second segment (6) and blood flows through side hole (2) and exits through distal hole (4). The outer diameter of first segment (5) and second segment (6) are the same in the illustrated embodiments. However, in alternate embodiments of the catheters disclosed herein, the outer diameter of segment (5) can be greater or less than the outer diameter of segment (6). Also, although one side hole is shown throughout the drawings of the various embodiments, it is also contemplated that more than one side hole for blood inflow can be provided in the bypass catheters disclosed herein. Similarly, multiple egress holes can be provided; however, when there is no intervening vascular branching a single end hole is preferred to maximize laminar flow, minimize turbulence, and maximize flow volume and rate.

The bypass catheter (1a) is introduced through an incision in a patient's vessel, most often percutaneously, and often directed through the vasculature to a target site by use of standard endovascular techniques, with the aid of wires, e.g. guidewires, and/or delivery catheters, often under fluoroscopic guidance. The catheter can be inserted over a guidewire extending through proximal opening (7) and lumen (17) of the catheter (1a) and out distal opening (4).

First or distal segment (5) in some embodiments has structure for anchoring device (1a) within the vessel so as to position and maintain side hole (2) at the desired location. This structure can include for example expandable wires which expand to at least the size of the inner diameter of the vessel to hold the device (1a) in place. Alternatively, an expandable balloon can be provided such as balloon (8) shown in FIG. 1, which is attached to first segment (5). The balloon (8) can also serve to regulate flow, and thereby help control contact of any delivered medication with any clot. The balloon (8) is inserted in a deflated collapsed position. Upon inflation via injection of fluid (liquid or gas) through a channel (15) in catheter (1a) which communicates with the interior of balloon (8), the balloon (8) expands from a collapsed condition to an expanded position to at least the inner diameter of the vessel to thereby anchor catheter (1a) in the desired position. Note the catheter (1a) can include a separate channel or lumen (15) (see FIG. 1A) for injection of inflation fluid, e.g. saline, to expand the balloon (8) or for passage of a wire or other elongated mechanism for expanding the wires in the embodiment wherein a mechanical expander is used instead of a balloon for anchoring the catheter (1a). In a preferred embodiment, the additional lumen is within or substantially within the wall of the catheter, thereby minimizing any obstruction within the primary central lumen, and maximizing blood flow through the bypass segment. The term substantially within (or substantially embedded in) the wall as defined herein means more than 75% of the lumen is within the wall either radially with respect to the wall or longitudinally along the length. The anchoring device, e.g., balloon (8), is shown positioned between side hole (2) and distal hole (4), but alternatively, can be positioned in other regions of the catheter, e.g., proximal of side hole (2) in second (proximal) segment (6). Note that anchoring structures can be provided on the other bypass catheters disclosed herein. In some embodiments, no anchor is provided.

Figure 1A:
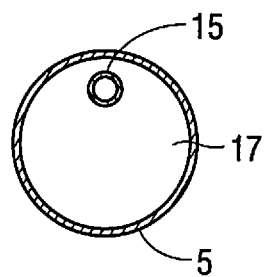
FIG. 1A is a transverse cross-sectional view of the catheter of FIG. 1.
Figure 1B:
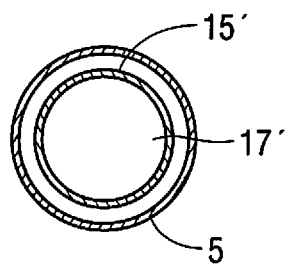
FIG. 1B is a transverse cross-sectional view of an alternate embodiment of the catheter of FIG. 1.
Figure 1C:
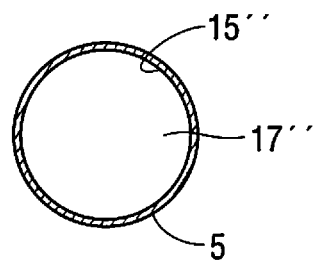
FIG. 1C is a transverse cross-sectional view of another alternate embodiment of the catheter of FIG. 1.

As shown in FIG. 1A, the lumen 15 is positioned within the central lumen 17. Alternatively, the lumen 15' (FIG. 1B), serving the same function as lumen 15, can be embedded or substantially embedded in the wall of the catheter segment 5. The primary central lumen for blood flow is designated by reference numeral 17'. Alternatively, the lumen 15" (FIG. 1C), serving the same function as lumen 15, can be adjacent the wall of the catheter segment 5 so it shares a wall of catheter segment 5. Primary central lumen for blood flow is designated by reference numeral 17".

The device 1a of the present invention is positioned such that side hole (2) is positioned to accept blood flow from the patient and direct the blood through the lumen (17) in the first segment (5) and out through distal hole (4), bypassing said blood flow past a blockage. As noted above, one side hole (2) is illustrated, however, it is also contemplated that more than one side hole (2) can be provided in catheter 1a, as well as in the other catheters described herein, to provide more than one entry passage for blood flow into the catheter at a region proximal of the vessel blockage.

In some embodiments, there is at least one additional third proximal end-hole, which has an external termination device attached, and remains outside the patient's body at all times. Aspiration can optionally be applied to the third proximal end-hole when desired, to remove clot and debris from the vessel.

In some embodiments, an additional lumen is positioned within or substantially within the wall of the catheter and can take a spiral or corkscrew course within the wall to get to (extend to) the balloon, thereby potentially improving the flexibility of the catheter. Similarly, any wiring within the device, e.g., within the wall or substantially within the wall, to transmit energy as in the embodiments described below, when present, can take a similar spiral or corkscrew course as well within the wall. Alternatively, in some embodiments the additional lumen(s) for delivery of fluids such as medication to the perforations and/or for inflating and deflating the balloon may course freely entirely through the intravascular portion of the single primary central lumen, except for attachments proximal to said perforations and balloon; in effect additional microcatheters coursing through the outer catheter, and attached only distally.

It should be noted that in some embodiments where there is an additional lumen that courses through the intravascular segment of the elongate body, the device can divide proximally into multiple lumens with independent outer walls, preferably outside of the patient's body. Preferably, each lumen ends at its proximal end-hole with an independent external termination device, such as a hub with a luer-lock or diaphragm.

The catheters of the present invention can include structure or features to prevent backflow of blood through the lumen 17. Three alternatives are discussed below which can be used independently or in combination or one or more and can be used with any of the embodiments of the bypass catheters disclosed herein.

FIG. 1 illustrates an embodiment employing valve (3) disposed within the primary central lumen at the juncture of second section (6) with side hole (2). The valve (3) can take various forms such as a leaf valve, flapper valve, etc. The valve can be configured to allow blood flow in one direction, i.e., a distal direction, which prevents flow in a proximal direction without any clinician intervention. Alternatively, the valve can be configured to be opened by intervention of a clinician. In the embodiment of FIG. 1 for example, once the device (1) is positioned in the desired position adjacent the blood clot to be treated, e.g., removed, valve (3) is closed by the user (clinician) to prevent blood entering side hole (2) from flowing back into said second segment (6). The valve can be controlled at a proximal region of the catheter (1), with the control attached by a wire or other elongated member to the valve. By closing the valve (3), the blood is thereby directed through first segment (5), through lumen (17) of segment (5) and out distal end hole (4), and allowed to perfuse the at-risk tissue. Alternatively, the valve can be in a default closed position and opened when a wire is passed through it, subsequently automatically closing when the wire is removed.

Figure 2:
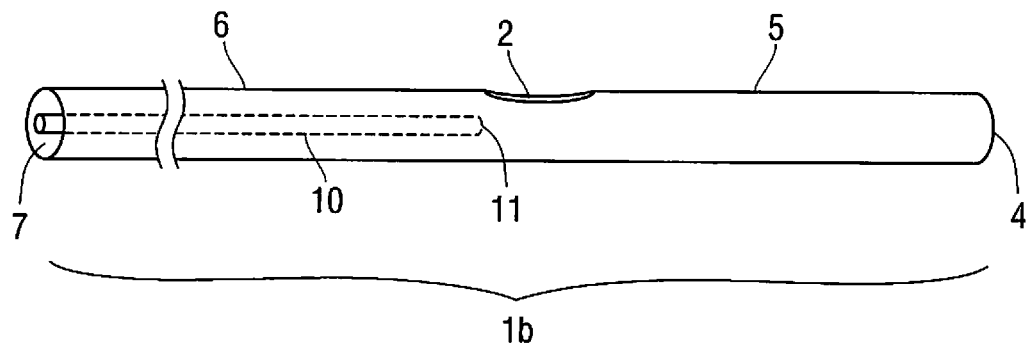
FIG. 2 is a side view of an alternate embodiment of the bypass catheter showing in dashed lines the inner diameter of the proximal segment.

In an alternate embodiment depicted in FIG. 2, instead of a valve, the inner diameter (10) of second segment (6) is less than the inner diameter of first segment (5). That is, the inner wall of second segment (6) is thicker to provide a smaller diameter lumen as compared to the lumen of segment (5). Inner diameter (10) terminates at inner hole (11). Inner hole (11) as shown is smaller than distal end hole (4). The differential of inner diameters acts to constrict backflow and direct blood through first segment (5) to and out end hole (4). In all other respects the catheter 1b of FIG. 2 is the same as catheter 1a of FIG. 1 and can optionally include an anchoring structure such as balloon (8) and a valve, but in preferred embodiments does not have a valve.

In some embodiments, both a valve (3) and a reduced inner diameter (10) and inner hole (11) are employed to constrict backflow of blood. As noted above, the valve can be configured to allow blood flow in one direction in its natural state or alternatively the valve can be manipulated by the clinician between an open position to allow blood flow, and a closed position to restrict blood flow when desired.

Figure 3:
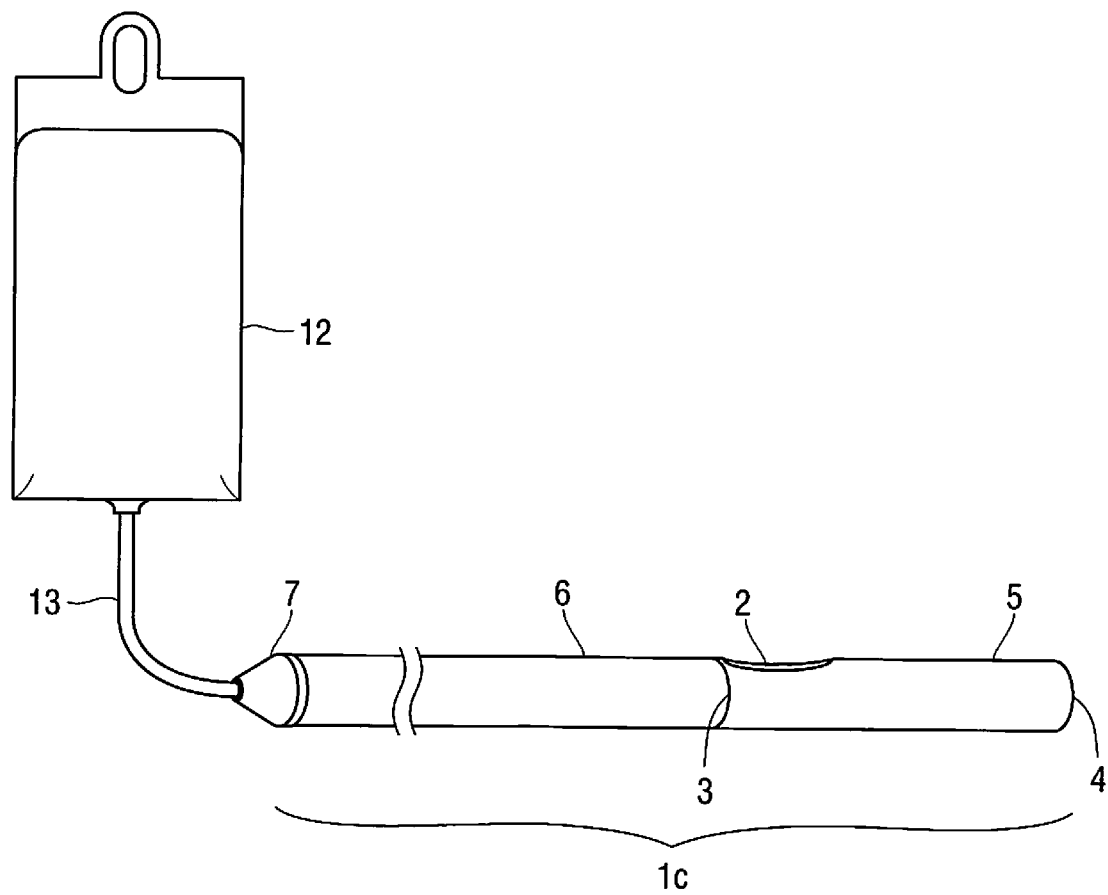
FIG. 3 is a side view of an alternate embodiment of the bypass catheter of the present invention shown connected to a pressurized fluid column via the third hole at the proximal end of the catheter.

In a still further embodiment depicted in FIG. 3, pressurized fluid may be introduced into second segment (6) to prevent the backflow of blood. FIG. 3 depicts device (1c) connected to pressurized fluid bag (12) interfacing with proximal end hole (7) via tubing (13), appropriate connectors, and an external termination device at the proximal end hole. Other sources of pressurized fluid are also contemplated such as an injection device. Proximal end hole (7) communicates second segment (6) through to first segment (5) via a lumen extending therein. The pressurized fluid bag (12) may be connected to a flow regulator which is outside the patient's body to allow the user of the device to control flow of fluid through the second segment (6). A pressure gauge can also be provided to regulate the pressure of the fluid delivered through the catheter. Like the catheter 1a of FIG. 1, the catheter 1c of FIG. 3 has a side hole (2) for entry of blood to bypass the blockage and distal hole (4) as described above.

The pressurized fluid may be used alone or in conjunction with valve (3) as shown in FIG. 3 and/or in conjunction with reduced diameter inner hole (11) to prevent backflow of blood through the segment (6). Stated another way, pressurized fluid, valve (3) and differential inner diameter (10) and inner hole (11) may all be used concurrently or only one or only two of these features can be used in the catheters disclosed herein. In some embodiments, the outer diameter of the proximal segment (6) and the distal segment 5 may vary as well. This may be particularly useful to limit the sheath size needed to introduce a larger diameter distal segment (6) to a lesion, when used in conjunction with an expandable sheath such as the e-sheath made by Edwards Lifescience.

In some embodiments, a balloon on the catheter or sheath (described below) can be provided which can be selectively inflated if there is a desire to arrest flow and or reverse flow during the clot treatment process, e.g., maceration process, to prevent showering of clots, or to aspirate clots and debris.

Figure 9:
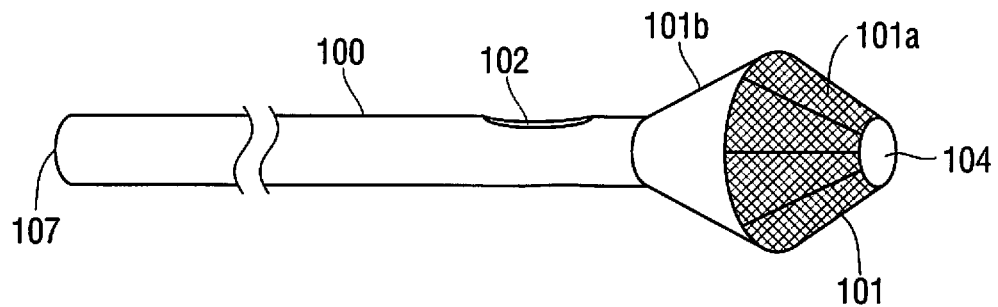
FIG. 9 is side view of an alternate embodiment of the bypass catheter of the present invention having a filter attached to the distal segment.
Figure 10:
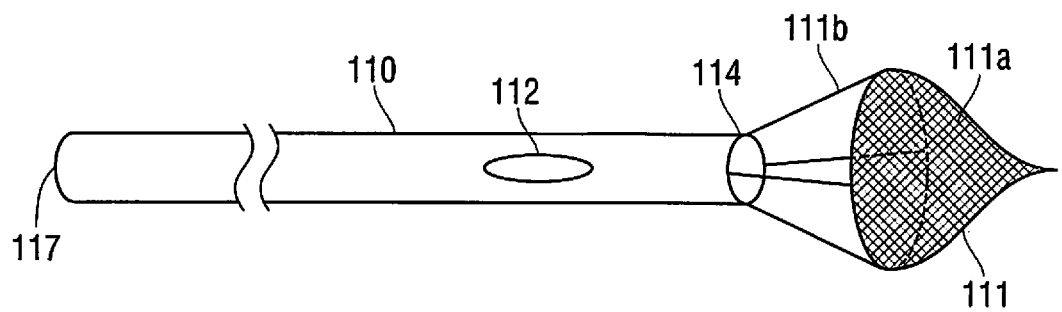
FIG. 10 is side view of an alternate embodiment of the bypass catheter of the present invention having a filter tethered to the distal end.
Figure 11:
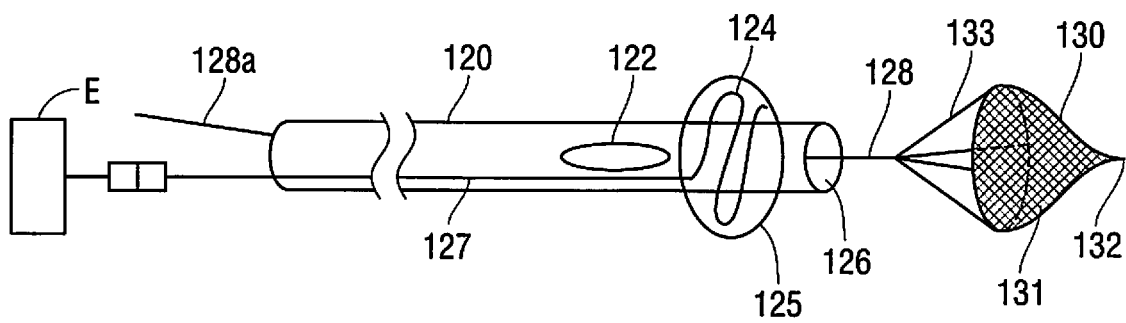
FIG. 11 is side view of an alternate embodiment of the bypass catheter of the present invention having a balloon with a plurality of electrodes connected thereon, the balloon shown in the inflated condition.

In some embodiments, the catheters can have a filter or distal protection device at a distal portion. FIGS. 9-11 illustrate three embodiments of such filter, mounted in different ways. Note these filters can be utilized with any of the embodiments of the devices (catheters) disclosed herein and FIGS. 9-11 illustrate some examples of such catheters.

In the embodiment of FIG. 9, filter 101 is attached to the distal end of catheter 100, terminating at end hole 104. Catheter 100, like the other catheters disclosed herein, has a proximal opening 107, a side hole 102 for blood inflow (like side hole 2 of FIG. 1) and a distal end hole 104 for blood exit in the bypass manner disclosed herein. In the embodiment of FIG. 10, filter 111 is tethered to the distal end of catheter 110 so it is positioned distal of distal hole 114. Wires 111b are attached to a distal region of the catheter 110, and extend distally thereof. Catheter 110, like the other catheters disclosed herein, has a proximal opening 117, a side hole 112 for blood inflow (like side hole 2) and a distal end hole 114 for blood exit in the bypass manner disclosed herein. The embodiment of FIG. 11 illustrates a distal filter 130 utilized with a catheter with energy emitters. FIG. 11 is discussed in more detail below.

Filters 101, 111 and 130 can have a wire, mesh, braid or other filtering material 101a, 111a, 131, respectively, to block/capture particles from traveling downstream in the vessel, while enabling blood flow therethrough. A plurality of wires 101b, 111b, 133 are expandable to move the filter 101, 111, 130, respectively, from a collapsed condition for delivery distal of the blockage to an expanded position. The filter can be self-expandable or can be manually controlled by a wire connected to wires 101b, 111b, 133 and actuable at a proximal region of the catheter outside the patient's body.

The semipermeable filter is attached circumferentially at or near the distal end of the catheter to minimize the risk of emboli during the procedure. The filter may have various modalities, to constrain and deploy it as desired. In some embodiments, the filter can be attached to a wire that extends through the entire lumen of the device and deploys distally within the vessel. The filter can be configured as shown or be of other shapes/configurations.

Figure 4:
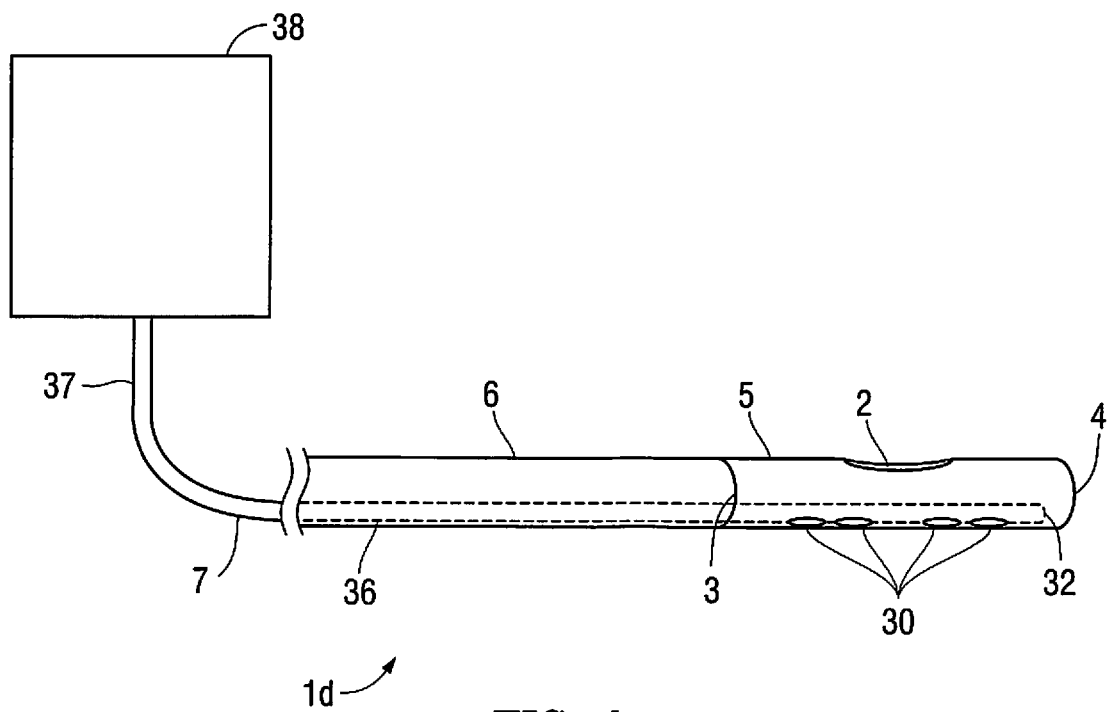
FIG. 4 is a side view of an alternate embodiment of the bypass catheter of the present invention having perforations for infusion of medication from the catheter into the vessel.
Figure 4A:
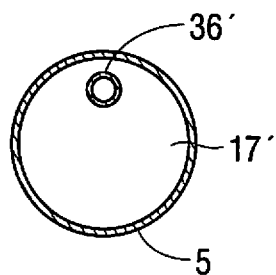
FIG. 4A is a transverse cross-sectional view of the catheter of FIG. 4.

FIG. 4 illustrates an alternate embodiment of the catheter of the present invention wherein first segment (5) is perforated with at least one perforation (30). Perforations (30) of bypass catheter 1*d* are end holes, i.e., exit holes, communicating with a separate lumen or channel (36) (FIG. 4A) within catheter 1*d*. Channel (36) provides an independent irrigation (fluid) channel extending to proximal end hole (7) and in communication with a controller (38) via tubing (37) for controlling the fluid flow through the channel (30). The fluid is introduced into the separate channel (36), flows through the channel (36) extending through segments (5) and (6) and exits perforations (30) to flow into the vessel and particularly the blood clot to dissolve vessel-clogging material of the clot. For example, the fluid may be a medication, for example a lytic such as Alteplase, which dissolves blood clots. The controller (38) is capable of controlling/regulating the flow of medication from controller through lumen (36) and out perforations (30) to effect the dissolution of clots near first segment (5). Alternatively, other methods such as hand injections via a syringe may be employed. The medication has the capability of softening and/or changing the chemical makeup of blood clots adjacent perforations (30) for purposes of dislocating and/or dissolving the clot(s) or other blockage. To enhance dissolution an energy source can be provided which is described in detail below in conjunction with FIG. 6.

One or more of the perforations (30) can be provided between the side hole 2 and distal hole 4 of the bypass catheter 1. Alternatively or additionally, one or more perforations (30) can be provided proximal of the side hole 2 as shown in FIG. 4. Fluid exiting from perforations (30) can affect proximal regions of the blood clot. Note in FIG. 4 the side hole (2) is shown in a middle (intermediate) region of segment (5), however, it should be appreciated that the side hole (2) can be provided along other regions of catheter 1*d*, such as in a proximal region of segment (5) as in the embodiment of FIG. 1. A valve 3 or other flow restricting structure can be provided.

Figure 4B:
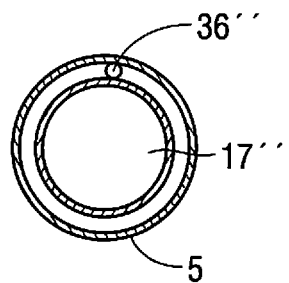
FIG. 4B is a transverse cross-sectional view of an alternate embodiment of the catheter of FIG. 4.
Figure 4C:
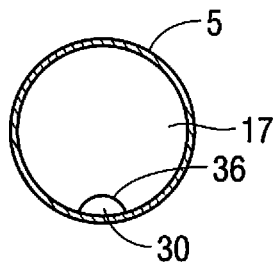
FIG. 4C is a transverse cross-sectional view of another alternate embodiment of the catheter of FIG. 4.

The device (1*d*) of FIG. 4 can be composed of concentric lumens wherein channel (36) for medication flow communicating with perforations (30) is centered within the lumen (17). In alternate embodiments, the channel is positioned within the primary lumen but off-center, and substantially along the wall of the catheter. In another embodiment shown in FIG. 4B, the fluid delivery lumen leading to the perforations courses substantially through the wall of the intravascular segment of the catheter. More specifically, in FIG. 4C, channel 36 is shown adjacent the wall of the catheter segment 5 so it has a common wall with the catheter. In the alternate embodiment of FIG. 4A, the channel 36' which functions like channel 36, is positioned off center within the primary central lumen 17' of catheter segment 5 which functions like lumen 17. In the embodiment, of FIG. 4C, the channel 36" which functions like channel 36, is embedded in the wall of the catheter segment 5. The primary central lumen which functions like lumen 17 is designated by reference numeral 17".

In some embodiments, perforations (30) communicate with the area between the internal surface of the outer lumen and the outer surface of the inner lumen 36, said gap extending from perforations (30) to proximal end hole (7) and communicating with the controller (38). This allows medication to be pumped from the controller (38) through the area between the internal surface of the outer lumen and the outer surface of the inner lumen and out perforations (30) to allow the infusion of medication to soften, lyse, or alter the composition of clots or blockages. In the preferred embodiment, the inner channel (or area between the internal surface of the outer lumen and the outer surface of the inner lumen) terminates at the most distal perforation (30) at end (32). Alternatively, the inner channel may terminate in the first segment (5) at or near the end hole (4). In alternative embodiments, there may be one or more slits along the catheter surface, instead of or in addition to said perforations, through which said fluid medication is delivered.

Figure 5:
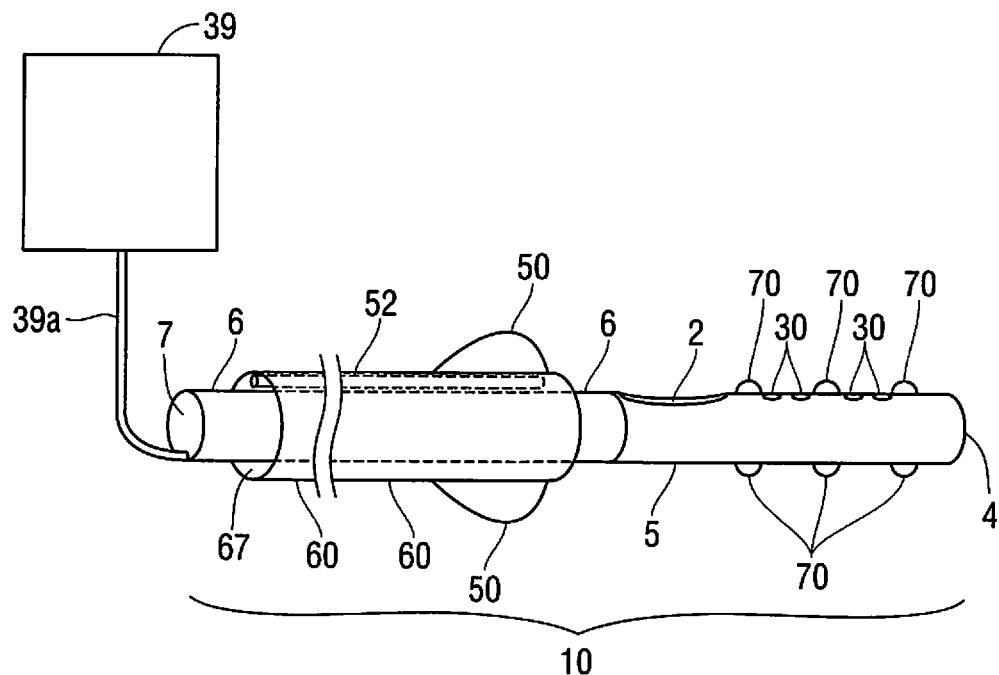
FIG. 5 is side view of an alternate embodiment of the bypass catheter of the present invention.

Referring now to FIG. 5, an alternate embodiment of the device of the present invention further includes rotating, macerating and irrigating elements. More particularly, bypass catheter 10 includes a slidable outer support sheath (60) having a proximal opening (67), macerating elements or loops (70), and/or perforations (30) used as irrigating elements to enable outflow of fluid such as medication for dissolving blood clots. The slidable outer support sheath (60) provides a hole covering member and is capable of snugly closing side hole (2) when first segment (5) is withdrawn (moved proximally) inside of said sheath (60) or sheath 60 is advanced (moved distally) to cover side hole (2) or both sheath 60 is moved distally and first segment (5) is moved proximally. Each of these variations can be considered relative movement. In any of these methods, such relative movement is utilized to effect opening (exposure) of side hole (2) and closing (covering) of side hole 2 as desired by the clinician. Movement of the sheath (60) is controlled at a proximal end and movement of the first segment (5) is controlled by movement of the catheter 10 also controlled at the proximal end. When side hole (2) is closed, aspiration of intravascular contents via end hole (4) can be accomplished by applying external aspiration at proximal end hole (7).

Figure 8:
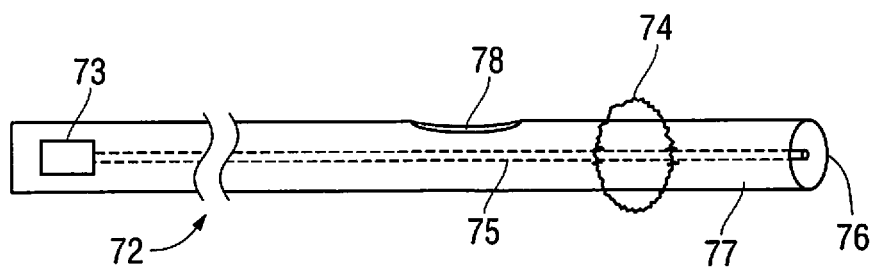
FIG. 8 is side view of an alternate embodiment of the bypass catheter of the present invention having a rotational mechanical thrombectomy device.

Macerating elements (70) extend radially from the catheter (10) and are preferably positioned between the side hole (2) and distal hole (4). Macerating elements (70) macerate the clot as the catheter 10 is rotated to rotate the elements (70). Such rotating can occur concurrently with infusion of medication through perforations (30) to also aid mixing or movement of the medication. Although shown in the form of loops (70), other macerating structure is also contemplated. In an alternate embodiment shown in FIG. 8, instead of the macerating element(s) rotatable by rotation of the catheter, the macerating element is rotated independent of the catheter. As shown in FIG. 8, the macerating element 74, in the form of a wire, extends radially from the bypass catheter 72 and is mounted on a rotating shaft 75. Shaft 75 extends through lumen 77 and can be manually rotated or alternatively rotated by a motor 73, positioned within the catheter, to break up the clot. During maceration, blood flows through side hole 78, through lumen 77 and exits distal and hole 76 to bypass the blood clot. Perforations like perforations 30 of FIG. 5 can be provided for fluid, e.g., medication injection. A sliding member, e.g., a sheath, can be provided to selectively cover side hole 78.

Turning back to FIG. 5, catheter (10) further includes an aspiration controller (39) communicating with proximal end hole (7) via tubing (39*a*). Such aspiration is utilized to effect backflow of blood through the catheter (10). More specifically, when the side hole (2) is uncovered by sheath (60), the catheter performs its bypass function with blood flowing through the side hole (2) and out the distal end hole 4 to bypass the vessel blockage in the same manner has side hole 2 and distal hole 4 of the aforedescribed embodiments. When side hole (2) is covered by the outer support sheath (60), and the aspiration is activated via controller (39), this results in changing the blood-flow bypass from side hole (2) through distal end hole (4) to instead redirecting the blood flow from distal end hole (4) out proximal end hole (7) due to aspiration controller (39) communicating with proximal end hole (7).

Device (10) can also include a backflow valve like valve (3) or other reverse flow restricting features/structure described herein. A balloon (50) can be provided, expandable by inflation fluid injected through a channel (52) in the catheter (10), to expand to a diameter equal to or slightly greater than the internal diameter of the vessel to provide an anchoring force to secure the catheter in position and/or to control flow in the vessel. Note the balloon (5) in the illustrated embodiments is proximal of the side hole (2) but can be positioned in other locations. Other mechanical anchoring elements can alternatively be provided as described above.

If the operator chooses to aspirate from distal end hole (4), the bypass catheter (10) can be pulled back (or the sheath (60) moved forward or both moved relative to each other) so that the side hole (2) is temporarily positioned within sheath (60), which is sized for a snug fit around bypass catheter (10), and aspiration force applied at proximal hole (7) will be transmitted to proximal end hole (4), provided valve (3), when provided, is open during said aspiration. It should be noted that for optimal use of this embodiment of the present invention, first segment (5) must fit snugly inside slidable outer support sheath (60) or at least provide a minimum gap so inflow of blood through side hole 2 is inhibited or completely restricted when sheath (60) is covering side hole (2).

It should be appreciated that in alternate embodiments, to close off the side hole (2), the hole covering member can be an inner member slidably disposed within the lumen of device (10) and can be moved distally, or the device 10 retracted proximally, or both moved relative to each other, so that the outer wall of the inner member covers the side hole 6, preferably sufficiently tight to reduce or close a gap between the outer wall of the inner member and the inner wall of the device 10 to restrict blood flow therein.

Figure 6:
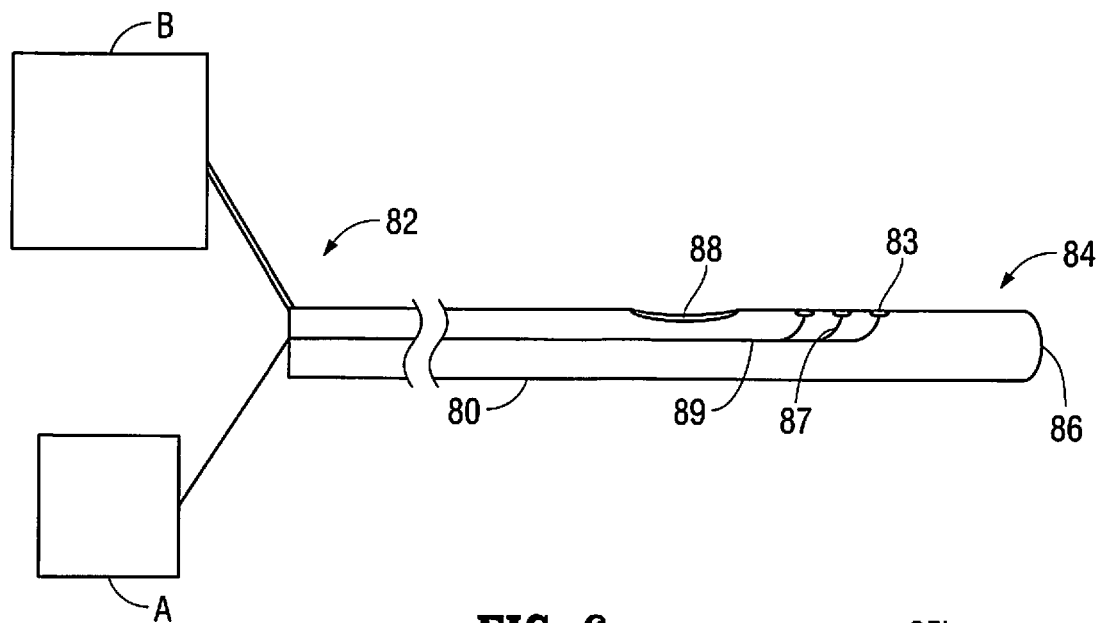
FIG. 6 is side view of an alternate embodiment of the bypass catheter of the present invention having ultrasonic energy emitters.
Figure 7:
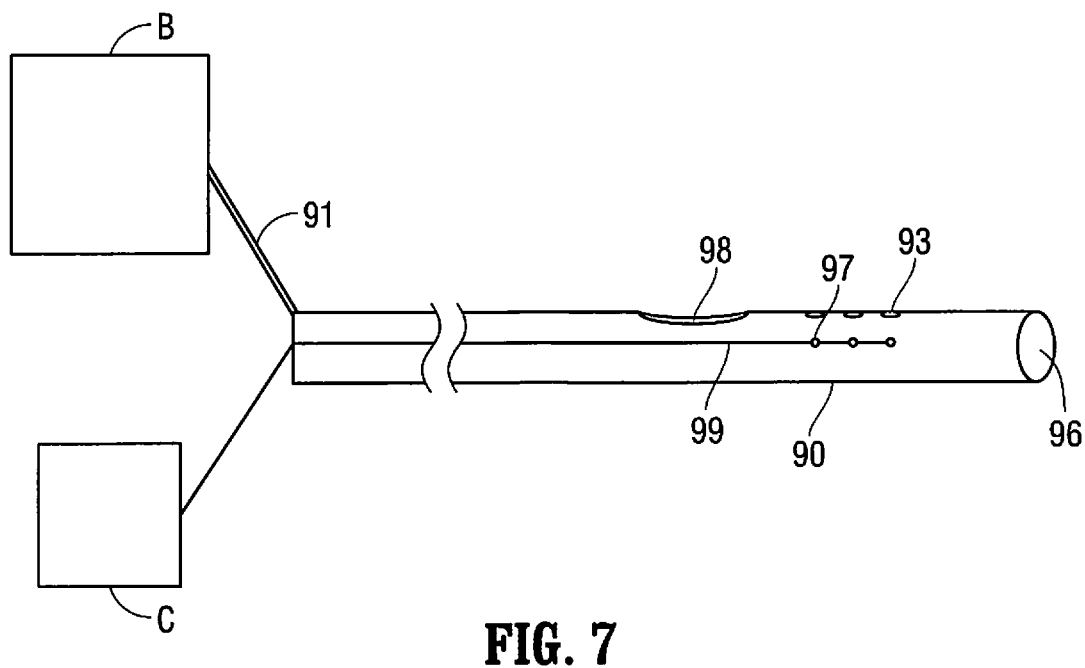
FIG. 7 is side view of an alternate embodiment of the bypass catheter of the present invention having a plurality of electrodes.
Figure 7A:
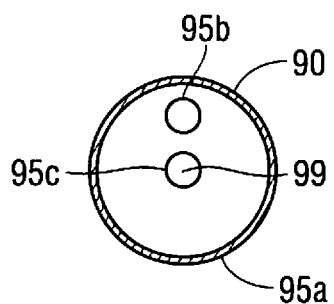
FIG. 7A is a transverse cross-sectional view of the catheter of FIG. 7.

FIGS. 6-7A illustrate alternate embodiments of the bypass catheter of the present invention wherein energy is applied to treat the blood clot, e.g., break up or dissolve the clot. The energy can be used in conjunction with clot dissolution drugs or alternatively used without such drugs relying on mechanical breakup of the blood clot. In some embodiments, ultrasound waves are transmitted. Various frequencies of ultrasound can be utilized. Some frequencies are optimized for clot dissolution, some frequencies are optimized for medication delivery into a clot, some frequencies are optimized for softening calcium, some frequencies are optimized for dissolving calcium, some frequencies are optimized for breaking up calcium and some frequencies are optimized for other uses.

Figure 6A:
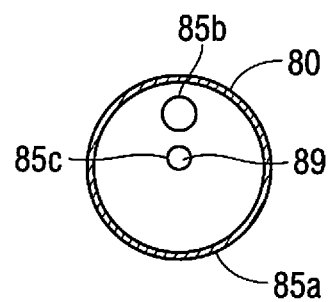
FIG. 6A is a transverse cross-sectional view of the catheter of FIG. 6.

Turning first to the device of FIG. 6, device (bypass catheter) 80 has a proximal end 82, a distal end 84 terminating in a distal exit (end) hole 86 and a side hole 88 in the outer wall of device 80. The bypass catheter 80 can be considered to have two segments or portions, either integral or separate joined components, as described above. The bypass catheter 80 in this embodiment has three channels (lumens): i) main channel 85a which enables blood entering through side hole 88 in the wall of the catheter 80 to flow out distal hole 86 to bypass the blood clot to provide for immediate perfusion, ii) channel 85b for injection of medication such as thrombolytics from fluid source B to dissolve the clot; and iii) channel 85c to contain the wire(s) 89 connecting the ultrasonic source A to the energy emitters (radiating elements) 87 disposed on, e.g., along, the catheter 80. Note that these three lumens 85a, 85b, 85c are provided by way of example since in alternate embodiments the wires 89 can be positioned in the fluid channel 85b in which case the catheter 80 would have two lumens instead of three. Alternatively, the wires 89 can be embedded or substantially embedded in a wall of the catheter 80. In a preferred embodiment both the wires and the additional lumen for fluid/medication delivery are both embedded fully or substantially within the wall of the intravascular segment of the catheter. This arrangement limits obstructions to flow of blood through the catheter in the bypass segment, thereby maximizing flow and perfusion of the distal vascular territory during vessel obstruction by a blockage and during vessel obstruction by an inflated balloon or other obstruction. FIG. 6A is a transverse cross-sectional view of the catheter 80 showing one possible arrangement of the lumens, however, it should be appreciated that other arrangements of the lumens and sizes of the lumens can vary from those shown.

Similar to the secondary lumens of FIGS. 1 and 4, several alternate embodiments (not pictured) are also possible, including various arrangements that may incorporate the secondary and tertiary lumens within or substantially within the wall of the elongate member. Alternatively, a secondary lumen may be within or substantially within the wall, and a tertiary lumen may course through the primary central lumen, or vice-versa.

The ultrasonic source A provides ultrasonic energy through wire(s) 89 to the energy emitters 87 so that the medication flow within the blood clot is enhanced. Note three energy emitters (also referred to energy emitting elements) are shown by way of example as a fewer number or an additional number of emitters can be provided as well as spacing along a length of the catheter 80 other than the spacing shown can be utilized. Moreover, the emitters 87 are shown positioned on one side of the catheter 80, in a longitudinal row, but additional emitters can be provided on other sides of the ultrasonic catheter, e.g., a series or longitudinal row of emitters on sides of the catheter spaced 180 degrees apart from emitters 87 shown. It is also contemplated that rather than longitudinally spaced as shown, a series of emitters can be radially spaced along an outer wall of the catheter 80. Any combination of arrangements, on the catheter and/or in the catheter, as well as on a balloon or multiple balloons and/or in a balloon and/or multiple balloons are contemplated as well. In the embodiment of FIG. 6, the energy emitters 87 are adjacent the openings 83 which deliver the medication or therapeutic agent to the blood clot. In alternate embodiments, the energy emitters can be spaced from the openings 83.

In preferred embodiments, the emitters 87 are positioned between the side hole 88 and distal hole 86 as shown. However, it is also contemplated that one or more energy emitters 87 can in lieu of or in addition be placed proximal of the side hole 88. This can provide ultrasonic energy to regions of the vessel proximal of the blood clot.

The wires 89 transmit to the emitters 87 the ultrasonic energy from the ultrasonic transducer A which is remote from the emitters 87 as shown schematically in FIG. 6A. However, in alternate embodiments, the emitters can include ultrasonic transducers (which convert electrical energy into ultrasonic energy) which are connected via wires to an electrical energy source. The ultrasonic energy can be emitted as continuous waves and/or pulsed waves and in various shaped waveforms, e.g. sinusoidal. Various frequencies are also contemplated. A microcontroller can be provided to control output. Alternative forms of energy are also contemplated.

Temperature sensor(s) can be provided on or adjacent the emitters 87 to monitor temperature of the radiating elements 87 or tissue during the procedure. Cooling elements can be provided.

In use, the bypass catheter 80 is inserted, typically minimally invasively, and advanced through the vessels for placement adjacent the blood clot so that the side hole 88 is positioned proximal of the blood clot and the distal end hole 86 is positioned distal of the blood clot as in the bypass catheters discussed above. This enables blood flow from proximal of the clot past the clot to provide immediate and, if desired, continuous, blood flow (and tissue reperfusion) during the procedure, and for as long as the catheter is left in place. The medication source is opened for medication flow either by a valve or switch on the catheter 80 or at a remote location on or adjacent the medication source B. The radiating elements (emitters) 87 are also activated, either by a switch on the catheter 80 or a remote switch, e.g., at the energy source, to apply energy via wires 89 to emitters 87 to apply ultrasonic energy to the blood clot and/or vessel (generating an acoustic field) to increase the permeability in the blood clot to thereby increase the efficacy of the medication in dissolving the blood clot as the medication is driven deeper into the clot. The activation enhances mixing of the medication via pressure waves and/or cavitation. The ultrasound energy and fluid injection can in some embodiments be synchronized to occur simultaneously. Alternatively, energy and fluid injection can be applied at separate time/intervals. During the ultrasonic energy application and medication delivery, the side hole 98 remains open so blood flow can continue distal of the clot, thereby avoiding blood disruption which can cause ischemia or other adverse conditions.

Note that in alternate embodiments, the ultrasound energy can be used without the drug injection. In such embodiments, the pulsed sound waves created by the ultrasonic energy source and emitted by the radiating elements 87 fragments the blood clots via cavitation to mechanically break up the clot. In alternative embodiments, rotational maceration can be used to mechanically break up the clot as well. As described previously, aspiration of clots and debris may optionally be performed as well. Combinations of the various techniques, either simultaneously and/or sequentially, may be performed as well.

In the alternate embodiment of FIG. 7, a pulse or shock wave generator C is connected to device (bypass catheter) 90. The generator produces shock waves that propagate through the blood clot to break up the clot. The pulse generator C can be utilized in some embodiments with medication to break up the clot. As noted above, alternatively the shock waves may be used to break up calcium or other hardenings.

More specifically, device 90 has one or more energy emitters 97 in the form of electrodes. As in device 80, device 90 has a distal exit (end) hole 96 and at least one side hole 98 in the outer wall of device 90. The bypass catheter 90 can be considered to have two segments or portions, either integral or separate joined components, as described above. The bypass catheter 90 in this embodiment has three channels (lumens) as in device 80: i) main channel 95*a* for fluid flow to bypass the blood clot; ii) channel 95*b* for injection of medication such as thrombolytics from fluid source B (via tubing 91) to dissolve the clot; and iii) channel 95*c* to contain the wire(s) 99 connecting the generator C to the electrodes 97 disposed on, e.g., along, the catheter 90. As described above with respect to lumens 85*a*, 85*b* and 85*c*, lumens 95*a*, 95*b*, 95*c* are provided by way of example and the variations described above for lumens 85*a*, 85*b* and 85*c*, and for the wires are fully applicable to lumens 95*a*, 95*b* and 95*c* of catheter 90 such as embedding in a wall of the catheter, centered, off-centered, etc.

Similar to the secondary lumens of FIGS. 1 and 4, several alternate embodiments are also contemplated, including various arrangements that may incorporate the secondary and tertiary lumens or electrodes or wires, or combinations thereof, within or substantially within the wall of the elongate member. Alternatively, a secondary lumen may be within or substantially within the wall of the catheter, and a tertiary lumen may course through the primary central lumen, or vice-versa.

The generator C provides voltage pulses (shock waves) transmitted by connectors or wire(s) 99 to the energy emitters (electrodes) 97 so that the shock waves propagate through the vessel and impinge on the blood clot to break up the clot. Note three energy emitters are shown by way of example as a fewer number or an additional number of emitters can be provided as well as spacing along a length of the catheter 90 other than the spacing shown can be utilized. Moreover the emitters 97 are shown positioned on one side of the catheter 90, in a longitudinal row, but additional emitters can be provided on other sides of the catheter, e.g., a series or longitudinal row of emitters on sides of the catheter spaced 180 degrees apart from emitters 97 shown. It is also contemplated that rather than longitudinally spaced as shown, a series of emitters can be radially spaced along an outer wall of the catheter 90.

The generator C can be used in conjunction with medication flow through perforations 93 as in device 80, and the energy emitters 97 can be positioned adjacent the openings 83 which deliver the medication or therapeutic agent to the blood clot or alternatively spaced from the openings 83.

In preferred embodiments, the emitters 97 are positioned between the side hole 98 and distal hole 96 as shown. However, it is also contemplated that one or more energy emitters 97 can in lieu of or in addition be placed proximal of the side hole 98. This can provide shock waves to regions of the vessel proximal of the blood clot.

A microcontroller can be provided to control output. Temperature sensor(s) can be provided on or adjacent the emitters 97 to monitor temperature of the electrodes or tissue during the procedure. Cooling elements can be provided.

The bypass catheter 90 can be inserted and used in the same manner as catheter 80 except for the transmission of shock waves so the description of use of device 80 is applicable to the use of device 90. During the energy application (and medication delivery if provided) the side hole 98 remains open so blood flow can continue distal of the clot, thereby avoiding blood flow disruption which can cause ischemia or other adverse conditions.

Note that in alternate embodiments, the energy can be used without the drug injection. In such embodiments, the shock waves created by the energy source and emitted by the electrodes 97 fragments the blood clots via cavitation to mechanically break up the clot.

In some embodiments, a balloon can overlie the energy emitters and the pulses can be provided within the balloon. In some embodiments, the energy emitters in addition to or instead of being within the balloon can overlie a balloon and the pulses can be provided within or on the balloon. These external emitters are shown in the embodiment of FIG. 11 wherein energy emitters 125, e.g., electrodes, overlie balloon 124 which is attached to catheter 120. Catheter 120 includes a side hole 122 and a distal end hole 126 for blood bypass as in the other bypass catheters disclosed herein. The catheter also has a primary lumen for blood flow and a secondary lumen for inflation of balloon 124. The balloon 124 and energy emitters 125 are positioned between the side hole 122 and end hole 124 and the emitters emit energy to the vessel. Energy source emitter E is connected to the emitters 125 via wires 127 in the same manner as the other energy emitters disclosed herein. The energy emitters can be in the various forms disclosed herein.

The catheter 120 in the illustrated embodiment has a filter 130, however, it should be appreciated that catheter 120 can be provided without a filter. The filter 130 is attached to a wire 128 extending the length of the catheter for access to the clinician outside the patient at region 128*a*. Wires 133 support the filter material 131, and the filter terminates at region 132. The filter 130 can alternatively be attached or tethered to the catheter 120 as in filters 101 and 111 of FIGS. 9 and 10, respectively.

A sheath such as sheath 60 of FIG. 5 (or inner blocking member) can be provided to selectively open and close the side hole 88, 98 of catheters 80, 90 respectively (or the side holes of any of the other catheters disclosed herein), if it is desired to discontinue blood flow past the clot. In some embodiments, the catheter 80, 90 can be connected to an aspiration source, such as aspiration source 39 described above in conjunction with the catheter of FIG. 5, to provide aspiration to effect backflow of blood through the catheter 80, 90 if and when desired.

Catheter 80, 90 (as well as the other catheter disclosed herein) can include structure such as described above, e.g., a valve, restricted opening, etc., to restrict back flow through the catheter. Catheter 80, 90 can also include anchoring structure such as wires or an inflatable balloon as in alternate embodiments described above.

Various forms of energy can be provided to the bypass catheter described herein such as ultrasonic energy, electrosurgical energy in the form of radiofrequency or microwave energy, etc. Furthermore, other types of energy including light or laser energy can be applied.

The energy can be applied between the side hole and distal hole so the clot can be treated while blood bypasses the clot as described above for immediate tissue reperfusion. That is, the various forms of energy and associated energy emitters or openings for energy emission in preferred embodiments are positioned between the side hole and distal exit hole. However, in alternate embodiments, instead of, or in lieu of energy applied between the side hole and distal hole, the energy emitters or openings can be positioned proximal of the side hole and/or have structure, e.g., an antenna or other energy emitting device, extending distal of the distal hole. When used with medication, the immediate reperfusion is beneficial as the clot lyses from lytic infusions over time.

In alternate embodiments, a mechanical thrombectomy device having at least one wire or other macerating structure is rotated by a motor positioned within the catheter such as in the embodiment of FIG. 8, or alternatively powered by a motor outside the catheter. The macerating element is mounted on a rotating shaft which upon actuation of the motor rotates about its axis so the macerating element breaks up the clot. The macerating element in preferred embodiments is positioned between the proximal and distal holes, however, it can alternatively be mounted in other locations. Alternatively, the macerating wires may be mounted on the catheter, and the entire catheter can be rotated for maceration.

In some embodiments, the catheter can have a complex shape to the second catheter segment, wherein rotation of the catheter itself can cause maceration. One example of such a complex shape is a sinusoidal shape.

The bypass catheters disclosed hereinabove have a side hole(s) and a distal hole(s) for blood to bypass the blood clot or other vessel blockage. In the alternate embodiment of FIG. 12, a torus balloon is provided with a passageway for blood flow when the balloon is inflated. One type of balloon which can be utilized is the bulging torus balloon disclosed in U.S. Pat. No. 10,328,246, the entire contents of which are hereby incorporated herein by reference, Other shape balloons are also contemplated.

An energy source such as those described herein can provide energy to emitters, e.g., electrodes, positioned on or in the bulging torus balloon. This can be used during valve lithotripsy while allowing egress of blood from the heart through the central hole of the balloon, during prolonged balloon inflation for prolonged contact with the valve, or similarly continued blood flow through a vessel during use in a vessel, without critically obstructing blood flow.

Figure 12:
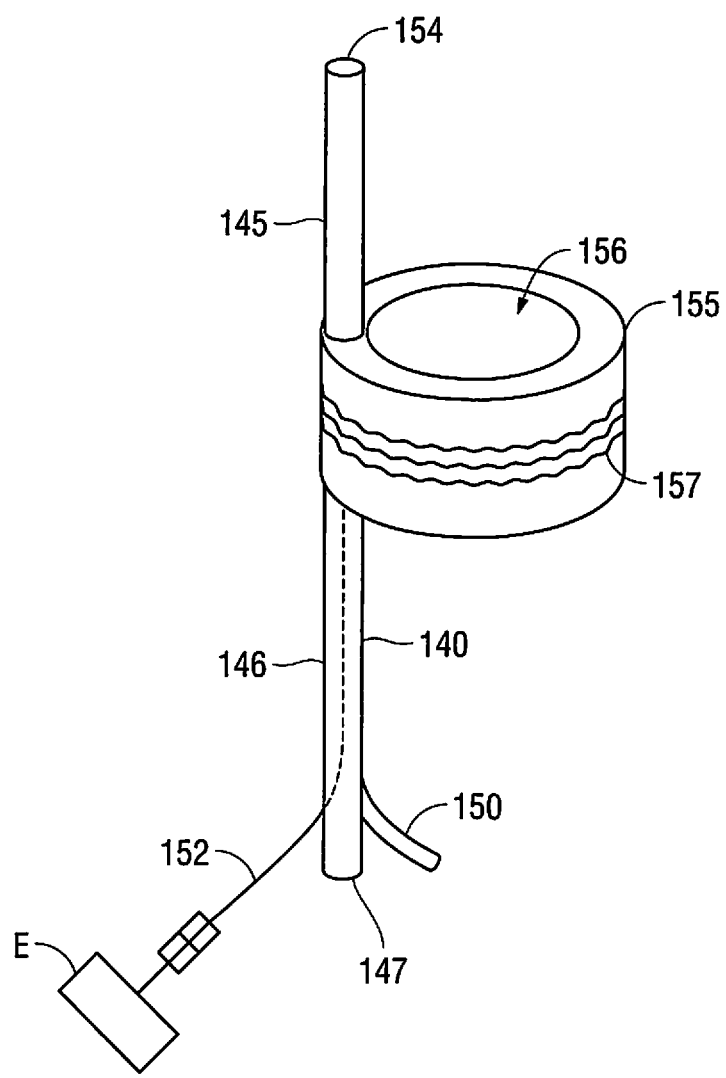
FIG. 12 is a side view of an alternate embodiment of a catheter of the present invention having a torus balloon having a plurality of electrodes connected thereon.

FIG. 12 illustrates catheter 140 having a torus balloon 155 mounted on the catheter. The torus balloon has a channel to receive the catheter, the catheter 140 extending therethrough as illustrated. The region of the catheter 140 distal of the balloon 155 is designated by reference numeral 145 and the region of catheter 140 proximal of the balloon 155 is designated by reference numeral 146. The catheter has a proximal opening 147 and a distal opening 154 fluidly connected by a lumen extending within the catheter 140. Port 150 provides for injection of fluid (liquid or gas) to inflate balloon 155.

The balloon 155 includes a passage, preferably a central passageway, parallel to a longitudinal axis of the catheter 140, to allow blood flow when the balloon 155 is inflated during the surgical procedure. A plurality of energy emitters 157 are positioned along the circumference of the balloon. The balloon 155 is offset from the longitudinal axis of the catheter 140 so the passage (passageway) is radially offset from the longitudinal axis of the catheter 140 and a majority (more than 50%) of the balloon 155 is offset to one side of the longitudinal axis. Inflation of the balloon 155 brings the energy emitters 157 closer to the vessel blockage for emission of energy to treat the blood clot or other vessel blockage. One or more energy emitters can be provided and they can be arranged in various arrays and various spacings about the circumference of the balloon, FIG. 12 providing an example of an arrangement of energy emitters. The energy emitters 157 can emit ultrasonic energy or other energy, and at various frequencies, as in the other energy emitters disclosed above. Connector 152, e.g., one or more wires, connects the energy emitters 157 to external energy source F of the system. The energy emitters 157 can be positioned on the outer wall (circumference) of the balloon, or alternately extending onto an outer surface of the balloon from within the balloon or alternately inside (within) the balloon or within the balloon but exposed via one or more openings in the balloon wall.

In use, the torus balloon is introduced across a valve (or other targeted site), the balloon 155 is inflated, energy is applied to the energy emitters from the energy source over a period of time, the emission of energy is then stopped, the balloon deflated and the catheter is removed. In some embodiments, these steps are repeated two or more times. When inflated to fill the vessel lumen, flow of blood continues through the opening in the balloon.

In some embodiments, the balloon is inflated such that the energy emitters are in contact with the target tissue, e.g., the blockage or calcifications in the lumen of the vessel. In other embodiments, when inflated, the energy emitters are spaced from (out of contact) with the target tissue.

In some embodiments, such a catheter mounted torus balloon for energy delivery system can have a single lumen, which can allow passage of wire, fluid injections, and inflation and deflation of the balloon. In other embodiments, the catheter can have a single catheter lumen exclusively (solely) for inflation of the torus balloon. In other embodiments, the catheter can have more than one catheter lumen. There may be a single balloon or multiple balloons. The balloon, e.g., the torus balloon, may be on any segment of the catheter.

Catheter 140 can have a filter at a distal end as in the catheters described above.

The balloon 155 catheter 140 is capable of prolonged inflation within cardiac valve, a vessel or other regions without critically obstructing outflow/blood flow. Without the opening in the balloon, blood flow would be blocked which has adverse consequences if cut off for a long period of time, especially in surgical procedures such as cardiac valve procedures. Note that the bypass catheters disclosed herein, e.g., the bypass catheters having balloon mounted or carried energy emitters, are likewise capable of prolonged inflation within the cardiac valve, a vessel or other regions without critically obstructing outflow/blood flow as the blood flows into the side hole and exits the distal hole. The torus balloon catheters and the bypass catheters disclosed herein can be used for intravascular or intraluminal lithotripsy to break down calcium via the energy emitters mounted or carried by the balloon while providing a channel/passage for blood flow.

Conceptually when a valve is stenotic, the outer portions of the leaflets fuse, and the remaining hole is narrowed. When a TAVR (endovascular valve replacement) is performed, this narrowed valve is stretched open, either with a balloon or a self-expanding valve. But if the fused section of the valve is highly calcified, the valve and adjacent tissue and/or aortic root can crack when it is stretched, which is usually fatal. The catheters of the present invention can be utilized to soften the calcium with lithotripsy before the TAVR so it can protect against this catastrophic complication. If the balloon is only in the small hole, the contact area for the lithotripsy is very limited. In contrast, if the surface area can be increased, calcifications can be reduced, The catheters of FIGS. 14-15 achieve this by providing an increased surface area for lithotripsy. These catheters have energy emitters mounted on balloon portions which are placed on opposing sides of the valve.

Figure 15:
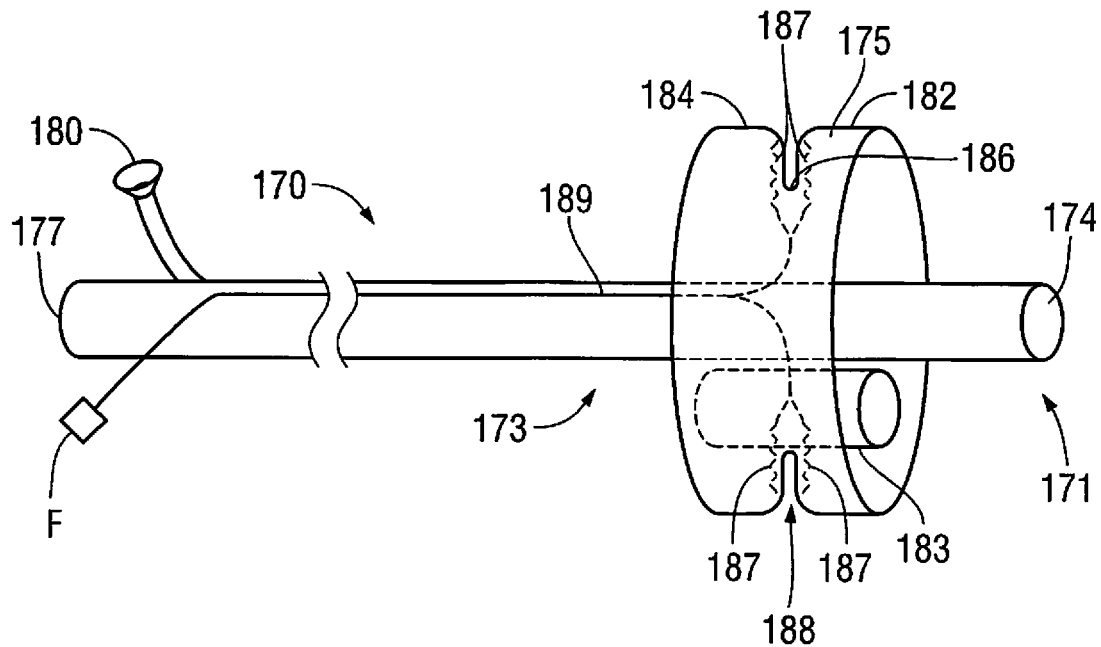
FIG. 15 is a side view of an alternate embodiment of a catheter of the present invention having a torus balloon with a narrow waist and a plurality of electrodes connected thereon.

More specifically, in the embodiment of FIG. 15 catheter 170 has a torus balloon 175 mounted on the catheter 170 and extending radially therefrom. Like torus balloon 155 of FIG. 12, the torus balloon 175 has a channel to receive the catheter, the catheter 170 extending therethrough as illustrated. The region of the catheter 170 distal of the balloon 175 is designated by reference numeral 171 and the region of catheter 170 proximal of the balloon 175 is designated by reference numeral 173. The catheter 170 has a proximal opening 177 and a distal opening 174 fluidly connected by a lumen extending within the catheter 170. Port 180 provides for injection of fluid (liquid or gas) to inflate balloon 175.

The balloon 175 includes a passage, like balloon passage 156 of FIG. 12, preferably a central passageway, parallel to a longitudinal axis of the catheter 170, to allow blood flow when the balloon 175 is inflated during the surgical procedure. The balloon 175 can include a tubular member 183 with proximal and distal openings forming the passageway through the balloon 175 for blood flow through the balloon 175. The balloon 175 is offset from the longitudinal axis of the catheter 170 so the passage (passageway) is radially offset from the longitudinal axis of the catheter 170 and a majority (more than 50%) of the balloon 175 is offset to one side of the longitudinal axis.

The balloon 175 has a first or distal portion 182 and a second or proximal portion 184 and an intermediate portion 186 between the first and second portions 182, 184. The intermediate portion 186 forms a waist or narrowed portion with a gap 188 between the first and second portions 182, 184. That is, a transverse dimension of the intermediate (narrowed) portion 186 is less than a transverse dimension of the first portion 182 and the second portion 184. In this manner, the first and second portions 182, 184 can be placed on opposing sides of the valve as described below.

A plurality of energy emitters 187 are positioned along the circumference of the balloon 175. In the illustrated embodiment, the energy emitters 187 on the distal portion 182 face the proximal portion 184 of balloon 175 and the energy emitters 187 on the proximal portion 184 face the distal portion 182. Note one or more energy emitters can be provided on each portion 182, 184. Further note that the energy emitters 187 can be positioned in other arrangements/arrays, other spacings and in other locations of the balloon 175. Inflation of the balloon 175 brings the energy emitters 157 closer to the valve for emission of energy to reduce calcium. Thus, FIG. 15 provides an example of an arrangement of energy emitters. The energy emitters 177 can emit ultrasonic energy or other energy, and at various frequencies, as in the other energy emitters disclosed above. In some embodiments, the balloon 175 (and balloon 195 described above) is inflated such that the energy emitters are in contact with the target tissue, e.g., the blockage or calcifications in the lumen of the vessel. In other embodiments, when inflated, the energy emitters are spaced from (out of contact) with the target tissue.

Connector 189, e.g., one or more wires, connects the energy emitters 187 to external energy source F of the system. The energy emitters 187 can be positioned on the outer wall (circumference) of the balloon, or alternately extending onto an outer surface of the balloon from within the balloon or alternately inside (within) the balloon or within the balloon but exposed via one or more openings in the balloon wall.

In use, the torus balloon 175 is introduced across a valve (or other targeted site), such as the cardiac valve. The balloon 175 is positioned such that distal portion 182 is on a first side of the valve and the proximal portion 184 is on the second side of the valve (e.g., to straddle the valve) and the narrowed waist portion is in the valve orifice. The valve, e.g., valve leaflets, can extend into the gap 188. In some embodiments, the expanded balloon portions 182, 184 are spaced slightly from the sides of the valve, i.e., the valve leaflets; in other embodiments, the balloon portions 182, 184 are in contact with the sides of the valve, i.e., the valve leaflets; and in other embodiments, the balloon portions 182, 184 form kissing sides and press against both sides of the valve, i.e., the valve leaflets.

The balloon 175 is inflated, energy is applied to the energy emitters 187 from the energy source over a period of time. The configuration of the balloon (and placement of energy emitters) increases the surface area of tissue the balloon is contacting and thereby significantly decreases the load of brittle calcium in the entire valve and surrounding tissue. When inflated, the balloon 175 fills the vessel lumen, however flow of blood continues through the opening (passage) in the balloon 175.

After application of energy, the emission of energy is then stopped, the balloon deflated and the catheter is removed. In some embodiments, these steps are repeated two or more times.

Figure 14:
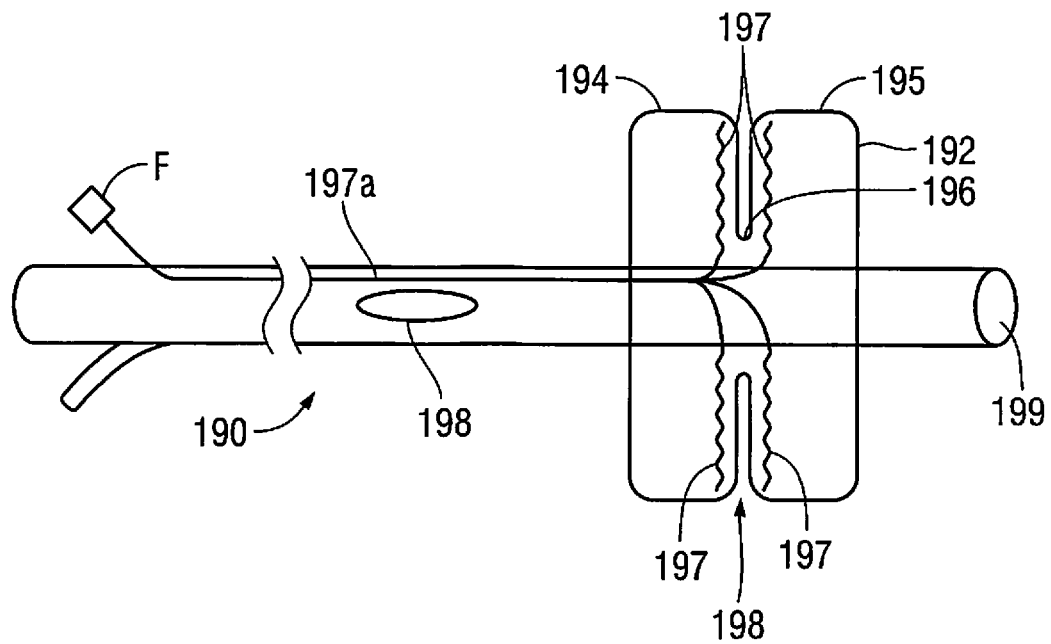
FIG. 14 is a side view of an alternate embodiment of a bypass catheter of the present invention having a torus balloon with a narrow waist and a plurality of electrodes connected thereon.

In the embodiment of FIG. 14, the torus balloon 195 of catheter 190 is similar to torus balloon 175 in that it has first or distal portion 192 and a second or proximal portion 194 and an intermediate portion 196 between the first and second portions 192, 194. The intermediate portion 196 forms a waist or narrowed portion with a gap 198 between the first and second portions 192, 194. That is, a transverse dimension of the intermediate (narrowed) portion is less than a transverse dimension of the first portion 192 and the second portion 194. In this manner, the first and second portions 192, 194 can be placed on opposing sides of the valve leaflets in the same manner as balloon 175 described above. Balloon 195 is centered with respect to the longitudinal axis of the catheter 190, although in alternate embodiments it can be offset from the longitudinal axis. In this embodiment, rather than a passageway through the balloon as in balloon 175, the catheter 190 is a bypass catheter similar to the catheter of FIG. 1 in that it has a side hole 198 (like side hole 2) and distal end hole 199 (like end hole 4) so that blood flows into the side hole 198, through the lumen in catheter 190 and exits the distal end hole 199 in the same manner as the bypass catheters described herein. Catheter 190 has energy emitters 197 that are positioned in the same manner as energy emitters 187 of catheter 170 and therefore the discussion of energy emitters 187, e.g., the arrangements, spacing, location with respect to the balloon, and alternatives thereof, are fully applicable to energy emitters 197. Connector 197a connects the energy emitters 197 to an external energy source F.

The catheter 190 is used in a similar manner as balloon 175 with regard to tits placement with respect to the valve, e.g., cardiac valve, and therefore the discussion of use of catheter 170, and its alternatives, is fully applicable to catheter 190, the difference being that in catheter 170 blood flows during the surgical procedure thorough the passageway in the balloon 175 and in catheter 190 blood flows during the surgical procedure through the side hole 198, lumen and distal hole 199 so that flow is not critically obstructed while the balloon is inflated.

Figure 16:
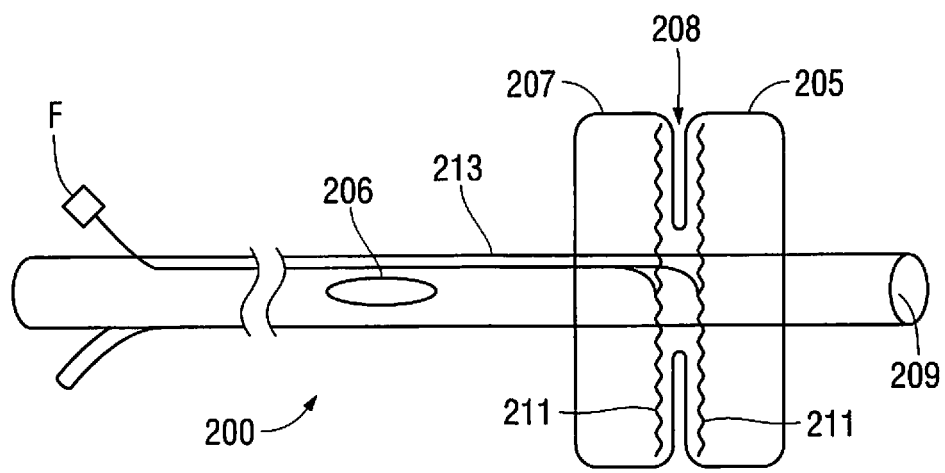
FIG. 16 is a side view of an alternate embodiment of a catheter of the present invention having two torus balloons, each having a plurality of electrodes connected thereon.

In the alternate embodiment of FIG. 16, bypass catheter 200 has two torus balloons 205, 207 rather than a single torus balloon, The proximal torus balloon 205 is placed on one side of the valve leaflets and the distal torus balloon 207 is placed on the other side of the valve leaflets. The space (gap) 208 is formed by the spacing of the two balloons 205, 207 rather than by a narrowed portion of the single balloon 195 of FIG. 15. The balloons 205, 207 each have one or more energy emitters 211 facing the other balloon, with connector 213 connecting the energy emitters to the external energy source F. The catheter 200 functions in the same manner as catheter 190 with the placement of the balloons the same as described above (one on each side of the valve) and blood flowing through side hole 209b, the lumen of the catheter 200 and exiting distal end hole 209 during inflation of the balloons in the same manner as catheter 190.

Note that shapes other than torus shaped balloons described herein could be utilized to treat the valves as described above.

The balloons 175 and 195 can have a figure eight configuration.

Note the catheter of FIGS. 15-17 are described for use with valve such as cardiac valve, but can be used to treat other area/tissue of a patient, while maintaining blood flow.

Figure 13:
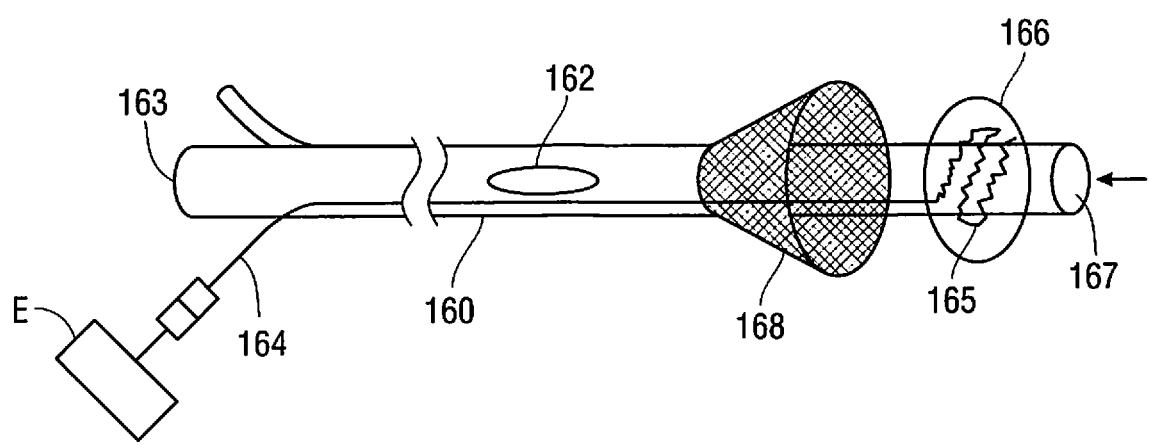
FIG. 13 is a side view of an alternate embodiment of catheter of the present invention for retrograde flow.

In some embodiments of the devices disclosed herein, when the device is introduced from a retrograde "upstream" approach blood may flow through the device in the opposite direction. This is depicted in FIG. 13 wherein blood flows through distal opening 167 of catheter in the direction of the arrow and can exit side hole 162 and/or proximal hole 163. The catheter 160 can include a balloon 166 with energy emitters connected via wire 164 to an external energy source E as in the aforedescribed embodiments. Catheter 160 can also include a filter 168 as in the embodiments described above.

The catheters of the present invention are preferably placed in a minimally invasive manner, most often percutaneously, e.g., through the femoral artery or radial artery, and advanced endovascularly (through the vasculature) to the target tissue site, e.g., adjacent the blood clot. The catheters are configured for temporary placement and are removed after the procedure. The catheters can alternatively be left in place over a period of time.

Although disclosed for treating blood clots, the catheters disclosed herein can be used to break up or dissolve and/or deliver medications to other regions of the body for performing other surgical procedures wherein immediate reperfusion, continuous and/or controlled blood flow is desired during the surgical procedure. It is ideally adapted for any luminal structures that may have a blockage. It can be used in human, animals, or even in pipes or similar structures.

It will be understood that the above particular embodiments are shown and described by way of illustration only. The principles and the features of the present disclosure may be employed in various and numerous embodiments thereof without departing from the scope and spirit of the disclosure as claimed. The above-described embodiments illustrate the scope of the disclosure but do not restrict the scope of the disclosure.

What is claimed is:

1. A catheter for intraluminal lithotripsy comprising:
    a) an outer wall;
    b) at least one balloon extending radially with respect to the outer wall, the at least one balloon having a first portion, a second portion proximal of the first portion and an intermediate portion between the first and second portions, wherein a transverse dimension of the intermediate portion is less than a transverse dimension of the first and second portions;
    c) a first lumen extending therein;
    d) at least one energy emitter for emitting energy to break down or soften calcium, the at least one energy emitter mounted on the at least one balloon;
    e) a connector connecting the at least one energy emitter to an external energy source, the connector extending through the catheter;
    f) a first hole at a distal portion positioned distal of the at least one balloon and a second hole spaced proximally from the first hole and positioned proximal of the at least one balloon and positioned in a side of the outer wall, wherein blood flows through the second hole, through the first lumen and exits the first hole while the balloon is inflated and energy is emitted by the at least one energy emitter.

2. The catheter of claim 1, wherein the at least one balloon is a torus balloon.

3. The catheter of claim 2, wherein the catheter is capable of prolonged inflation of the torus balloon within a cardiac valve, without critically obstructing cardiac outflow.

4. The catheter of claim 2, wherein the at least one energy emitter includes at least one energy emitter on the second portion of the torus balloon facing the first portion and at least one energy emitter on the first portion of the torus balloon facing the second portion.

5. The catheter of claim 4, wherein the first and second portions are configured to press against opposing sides of a cardiac valve of a patient.

6. The catheter of claim 2, wherein the intermediate portion of the torus balloon forms a waist portion creating a gap between the first and second portions of the torus balloon.

7. The catheter of claim 6, wherein the waist portion is configured for positioning in an orifice of a cardiac valve of a patient and the first and second portions of the torus balloon press against sides of the cardiac valve.

8. The catheter of claim 2, further comprising a filtering member positioned distal of the torus balloon to capture particles.

9. The catheter of claim 2, wherein the at least one energy emitter applies ultrasonic energy.

10. The catheter of claim 1, wherein the at least one balloon has an opening to provide a passage for blood therethrough.

11. The catheter of claim 10, wherein the at least one balloon is offset from a longitudinal axis of the outer wall so a majority of the at least one balloon is offset to one side of the longitudinal axis, and the passage is parallel to the longitudinal axis.

12. The catheter of claim 11, wherein the at least one balloon has a channel to receive the outer wall, the channel radially spaced from the opening in the at least one balloon.

13. The catheter of claim 11, wherein the at least one balloon has a figure eight configuration.

14. The catheter of claim 1, further comprising an axially slidable member slidable relative to the outer wall, the outer wall and slidable member relatively movable to selectively cover and expose the second hole, wherein covering of the second hole restricts flow of blood through the second hole.

15. The catheter of claim 1, further comprising a valve to restrict retrograde blood flow through the first lumen.

16. A method of valve lithotripsy comprising the steps of:
a) inserting the device of claim 1;
b) positioning the at least one balloon adjacent a cardiac valve of a patient so the first portion presses and faces a first side of the cardiac valve and the second portion faces a second opposing side of the cardiac valve and the intermediate portion is positioned in an orifice of the cardiac valve; and
c) applying energy to the at least one energy emitter to apply energy to the first and second sides of the cardiac valve to break down or soften calcium;
d) wherein the at least one balloon is a torus balloon and the catheter has a first hole at a distal portion positioned distal of the torus balloon and a second hole spaced proximally from the first hole and positioned proximal of the torus balloon and positioned in a side of the outer wall, wherein blood flows through the second hole, through the first lumen and exits the first hole while the torus balloon is inflated to bypass the cardiac valve.

17. The method of claim 16, wherein the at least one balloon is a torus balloon and is offset from a longitudinal axis of the outer wall and has an opening offset from the longitudinal axis of the outer wall for passage of blood therethrough.

18. The method of claim 16, wherein the torus balloon is inflated to fill a lumen of a vessel and the first portion presses against the first side of leaflets of the cardiac valve and the second portion presses against the second side of the leaflets of the cardiac valve, and blood bypasses the inflated torus balloon as the at least one energy emitter applies energy to the first and second sides of the cardiac valve leaflets.

* * * * *